United States Patent [19]

Bundy

[11] 4,123,463
[45] Oct. 31, 1978

[54] 2-DECARBOXY-2-ALKYLKETONE PROSTAGLANDINS

[75] Inventor: Gordon L. Bundy, Portage, Mich.

[73] Assignee: The Upjohn Company, Kalamazoo, Mich.

[21] Appl. No.: 888,695

[22] Filed: Mar. 21, 1978

[51] Int. Cl.² ........................................... C07C 177/00
[52] U.S. Cl. ............................. 260/586 R; 260/590 C; 424/337
[58] Field of Search .................... 260/586 R, 590 C

[56] References Cited

U.S. PATENT DOCUMENTS

| | | | |
|---|---|---|---|
| 3,931,296 | 1/1976 | Hayashi et al. | 260/514 D |
| 3,953,435 | 4/1976 | Hayashi et al. | 260/240 R |
| 3,978,229 | 8/1976 | Matsumoto et al. | 424/317 |

Primary Examiner—Gerald A. Schwartz
Attorney, Agent, or Firm—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

47 Claims, No Drawings

2-DECARBOXY-2-ALKYLKETONE PROSTAGLANDINS

BACKGROUND OF THE INVENTION

The present invention provides a novel composition of matter, 2-decarboxy-2-alkylcarbonyl-PG-type compounds. The present invention further provides for the use of these compounds as gastrointestinal cytoprotective agents. Moreover the present invention provides novel intermediates and processes for preparing such compounds.

The prostaglandins are a family of cyclic carboxylic acids, containing 20 carbon atoms. Typical of the prostaglandins is $PGF_2\alpha$, whose structure and carbon atom numbering are as depicted in formula I.

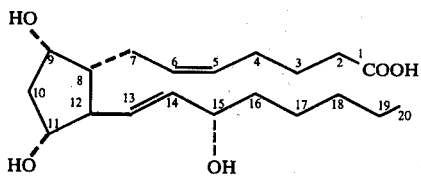

For a discussion of the prostaglandins and their pharmacological effects, see Bergstrom, et al., Pharmacol. Review 20:1, and references cited therein.

The prostaglandins, such as $PGF_2\alpha$ are all named according to the degree of unsaturation exhibited in the side chains at C-8 and C-12 and the functional groups and/or unsaturation present on the cyclopentane ring. Accordingly, $PGF_2\alpha$ exhibits two double bonds (C-5 and C-13), while the corresponding $PGF_1\alpha$ exhibits a single double bond at C-13. When the stereochemistry of $PGF_2\alpha$ at C-9 is reversed, the resulting prostaglandins are of the $PGF\beta$ series, e.g., $PGF_2\beta$. Likewise, a PGE compound such as $PGE_2$ is similar to $PGF_2\alpha$ as depicted above except that the C-9 hydroxy is replaced by an oxo.

The various prostaglandins all exhibit one or more centers of asymmetry and thus can exist in either optically active or optically inactive (racemic) form. For example, $PGF_2\alpha$ as depicted above contains five centers of asymmetry: C-8, C-9, C-11, C-12, and C-15. For formula I above and the various formulas hereinafter substituents of asymmetric carbon atoms above the plane of the cyclopentane ring are depicted by heavy solid lines (the beta configuration), while dotted lines represent substituents below the plane of the cyclopentane ring (the alpha configuration). Thus for $PGF_2\alpha$ the asymmetric centers are respectively of the alpha, alpha, alpha, beta, and alpha configurations. When wavy lines are employed hereinafter (~), the substituents thereby depicted are either in the alpha or beta configuration or in a mixture of alpha and beta configurations.

The side chain hydroxyl at C-15 of $PGF_2\alpha$ is in the "S" configuration according to the Cahn-Ingold-Prelog sequence rules. See J. Chem. Ed. 41:16 (1964). Also, Nature 212:38 (1966) provides a discussion of the stereochemistry of the prostaglandins. Expressions such as C-8, C-9, C-11, C-12, C-15, and the like will hereinafter refer to the carbon atom in any prostaglandin or prostaglandin analog which is in the position corresponding to the position of the same number in $PGF_2\alpha$ above.

For convenience hereinafter the use of the term prostaglandin ("PG") will mean the optically active form of the prostaglandin thereby referred to with the same absolute configuration as $PGF_2\alpha$ obtained from mammalian sources. The term prostaglandin-type of PG-type product, as used herein, will refer to any monocyclic or bicyclic cyclopentane derivative herein which is pharmacologically useful. The formulas as drawn herein which depict a prostaglandin-type product or an intermediate useful in the preparation of a prostaglandin-type product each represent a particular stereoisomer which is of the same relative stereochemical configuration as the corresponding prostaglandin obtained from mammallian sources, or the particular stereoisomer of the intermediate which is useful in preparing the above stereoisomer of the PG-type product. The term prostaglandin analog, as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type product herein, the term "prostaglandin analog" refers to the compound of that formula or a mixture comprising that compound and the enantiomer thereof.

In addition to the naturally-occurring prostaglandins, certain chemical analogs thereof have been prepared and are known in the art. Among the prostaglandin analogs known in the art are the PGD-type, $9\beta$-PGD-type, and 9-deoxy-9,10-didehydro-PGD-type compounds of U.S. Pat. Nos. 4,016,184; the PGC-type compounds of 3,993,686, the 9-deoxy-9-methylene-PGF-type compounds of 4,021,467 and 4,060,534; the 11-deoxy-PG-type compounds of 4,029,693 and 3,987,072; the $8\beta,12\alpha$-PG-type compounds of 3,979,483; the 2,2-difluoro-PG-type compounds of 4,001,300; the cis-4,5-didehydro-PG-type compounds of 4,032,561 and 3,933,889; the inter-phenylene-PG-type compounds of 4,020,097 and 3,997,566; the 5,6-didehydro-$PG_2$-type or 4,4,5,5-tetradehydro-$PG_1$-type compounds of 4,013,695; the 5-oxa-$PG_1$-type compounds of 3,931,279 and 3,864,387; the 4-oxa-$PG_1$-type and 3-oxa-$PG_1$-type compounds of 3,944,593,; the 13-cis-PG-type compounds of 4,026,909; the 13,14-didehydro-PG-type compounds of 4,029,681 and 4,018,803; the $\omega$-aryl-PG-type compounds of 3,987,087; the $\omega$-aryloxy-PG-type compounds of 3,864,387; the 16-alkyl-PG-type compounds of 3,903,131; the 16-fluoro-PG-type compounds of 3,962,293; and 15-methyl-PG-type compounds of 3,728,382.

While the naturally-occurring prostaglandins are carboxylic acids, numerous derivatives thereof are known in the art. For example, ester derivatives, including especially aromatic and phenacyl esters, are known in the art. See U.S. Pat. Nos. 3,069,332, 3,598,858, 3,979,440, and 3,984,062. Likewise, salts of these carboxylic acids are known in the art. See U.S. Pat. Nos. 3,069,332 and 3,958,858 cited above, as well as other references such as 3,657,327 and 3,888,916. Other derivatives of the prostaglandins, such as the amides thereof, are known in the art. See U.S. Pat. Nos. 3,853,941, 3,884,942, 3,903,299, 3,880,883, and 3,953,470.

Finally, there are also known macrocyclic lactone derivatives of the prostaglandins as is, for example, described by Corey, E. J. et al., JACS 97:653 (1975) and U.S. Pat. Nos. 3,931,206, 4,067,991, 4,049,648, 4,032,543, 4,045,449, and 4,049,678.

In addition to these various carbonyl-containing prostaglandin analogs, there are likewise known in the art acidic, non-carboxylic prostaglandin anlogs such as tetrazoles and sulfonates. See for example the 2-decarboxycarboxy-2-tetrazolyl-PG analogs described in U.S. Pat. Nos. 3,883,513, 3,932,389, 3,984,400, and 4,035,360. Also 2-decarboxy-2-sulfonyl-type compounds are described in U.S. Pat. No. 3,922,301.

Among the various other modifications at the C-2 position of the known prostaglandin analogs is the replacement of the carboxyl with an amine, as is for example described in U.S. Ser. No. 719,055, filed Aug. 30, 1976 and Derwent Farmdoc CPI No. 46957Y (abstracting Belgian Pat. No. 849,963).

Numerous references also describe primary alcohols corresponding to the known prostaglandins and analogs thereof as are described in U.S. Pat. Nos. 4,028,419, 4,055,602, 4,032,576, 3,931,207, 3,878,239, 3,966,792, 4,024,174, 3,962,312, 3,636,120, 3,723,528, 3,895,058, 3,954,881, 4,004,021, and 3,962,218. In addition to these 2-decarboxy-2-hydroxymethyl-PG compounds, there are known the corresponding C-2 aldehydes as described in U.S. Pat. Nos. 3,931,296 and 3,953,435. See also Derwent Farmdoc CPI No. 35953X and at 93049X for a description of further 2-decarboxy-2-carboxaldehyde-PG analogs. Finally, the C-2 acetals thereof are described at Derwent Farmdoc CPI No. 94924X.

SUMMARY OF THE INVENTION

The present invention particularly provides: a prostaglandin analog of the formula

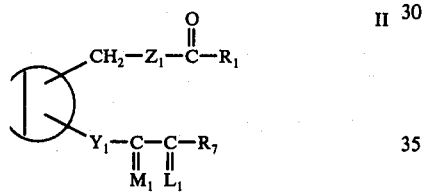

wherein D is

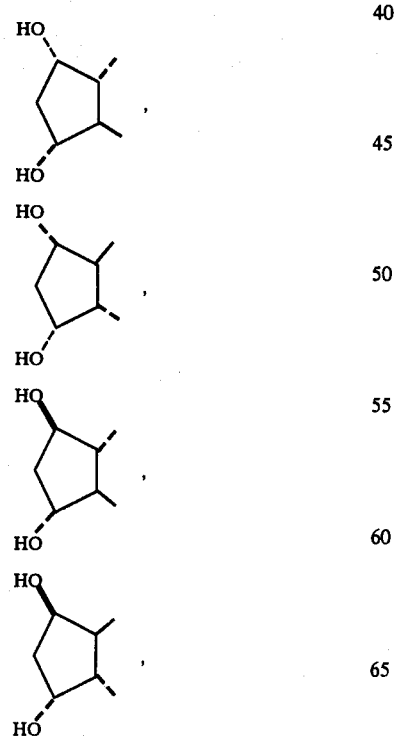

-continued

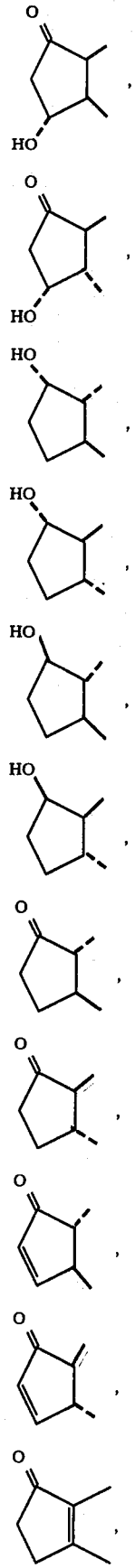

-continued

[structures with CH₂, HO groups on cyclopentane rings]

wherein R₁ is alkyl of one to 4 carbon atoms, inclusive;
wherein L₁ is

[structure with R₃, R₄]

a mixture of

[structure with R₃, R₄] and [structure with R₃, R₄], wherein R₃ and R₄ are hydrogen, methyl, or fluoro, being the same or different, with the proviso that one of R₃ and R₄ is methyl only when the other is hydrogen or methyl;
wherein M₁ is

[structure with R₅, OH] or [structure with R₅, OH], wherein R₅ is hydrogen or methyl;
wherein R₇ is (1) $-(CH_2)_m-CH_3$, (2) $-(CH_2)_h-$[phenyl with $(T)_s$], or (3) $-O-$[phenyl with $(T)_s$], wherein $h$ is zero to three, inclusive, wherein $m$ is one to 5, inclusive, $s$ is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;
wherein Y₁ is
(1) trans—CH=CH—
(2) cis—CH=CH—,
(3) —CH₂CH₂—, or
(4) —C≡C—; and
wherein Z₁ is
(1) cis—CH=CH—CH₂—(CH₂)$_g$—CH₂—,
(2) cis—CH=CH—CH₂—(CH₂)$_g$—CF₂—,
(3) cis—CH₂—CH=CH—(CH₂)$_g$—CH₂—,
(4) —(CH₂)₃—(CH₂)$_g$—CH₂—,
(5) —(CH₂)₃—(CH₂)$_q$—CF₂—,
(6) —CH₂—O—CH₂—(CH₂)$_g$—CH₂—,
(7) —(CH₂)₃—O—(CH₂)$_g$—CH₂—,
(8) —(CH₂)₃—O—(CH₂)$_g$—, (9) [phenyl]—O—(CH₂)$_g$—,

(10) [phenyl]—CH₂—(CH₂)$_g$—,

(11) —C≡C—CH₂—(CH₂)$_g$—CH₂—,

(12) —CH$_2$—C≡C—(CH$_2$)$_g$—CH$_2$—, or
(13) trans—(CH$_2$)$_2$—(CH$_2$)$_g$—CH=CH—,
wherein g is one, two, or three.

By virtue of the ketone function in the C-8 side chain, all of the novel prostaglandin analogs herein are named as 2-decarboxy-2-alkylcarbonyl-PG-type compounds. Accordingly, when R$_1$ is methyl, the novel prostaglandin analogs herein are named as 2-decarboxy-2-methylcarbonyl-PG-type compounds.

Further, the novel 2-decarboxy-2-alkylcarbonyl-PG-type compounds herein are further categorized according to their cyclopentane ring structure. This cyclopentane ring structure, providing a "parent-type" for each of the novel prostaglandin analogs herein is associated with the nomenclature indicated in the following table:

| CLASSIFICATION OF 2-DECARBOXY-2-ALKYLCARBONYL PG ANALOGS BY CYCLOPENTANE RING STRUCTURE | | |
|---|---|---|
| | Ring Structure | Nomenclature |
| A. | HO— (cyclopentane with HO) | PGFα-type compounds |
| B. | HO— | 8β,12α-PGFα-type compounds |
| C. | HO— | PGFβ-type compounds |
| D. | HO— | 8β,12α-PGFβ-type compounds |
| E. | O= | PGE-type compounds |
| F. | O= | 8β,12α-PGE-type compounds |
| G. | HO— | 11-Deoxy-PGFα-type compounds |
| H. | HO— | 11-Deoxy-8β,12α-PGFα-type compounds |
| I. | HO— | 11-Deoxy-PGFβ-type compounds |
| J. | HO— | 11-Deoxy-8β,12α-PGFβ-type compounds |
| K. | O= | 11-Deoxy-PGE-type compounds |
| L. | O= | 11-Deoxy-8β,12α-PGE-type compounds |
| M. | O= | PGA-type compounds |
| N. | O= | 8β,12α-PGA-type compounds |
| O. | O= | PGB-type compounds |
| P. | H$_2$C= | 9-Deoxy-9-methylene-PGF-type compounds |

-continued
CLASSIFICATION OF 2-DECARBOXY-2-ALKYLCARBONYL PG ANALOGS BY CYCLOPENTANE RING STRUCTURE

| | Ring Structure | Nomenclature |
|---|---|---|
| Q. | H₂C [structure] HO | 9-Deoxy-9-methylene-8β,12α-PGF-type compounds |
| R. | HO [structure] O | PGD-type compounds |
| S. | HO [structure] O | 8β,12α-PGD-type compounds |
| T. | HO [structure] O | 9β-PGD-type compounds |
| U. | HO [structure] O | 8β,9β,12α-PGD-type compounds |
| V. | [structure] O | 9-Deoxy-9,10-didehydro-PGD-type compounds |
| W. | [structure] O | 9-Deoxy-9,10-didehydro-8β,12α-PGD-type compounds |

Those novel prostaglandin analogs herein wherein $Z_1$ is cis—CH=CH—CH₂—(CH₂)$_g$—CH₂— or cis—CH=CH—CH₂—(CH₂)$_g$—CF₂— are named as PG₂-type compounds. The latter compounds are further characterized as 2,2-difluoro-PG-type compounds.

Further when $Z_1$ is —(CH₂)₃—(CH₂)$_g$—CH₂— or —(CH₂)₃—(CH₂)$_g$—CF₂, wherein g is as defined above, the compounds so described are PG₁-type or 2,2-difluoro-PG₁-type compounds.

When $Z_1$ is —CH₂—O—CH₂—(CH₂)$_g$—CH₂— the compounds so described are named as 5-oxa-PG₁-type compounds. When $Z_1$ is —(CH₂)₂—O—(CH₂)$_g$—CH₂—, wherein g is as defined above, the compounds so described are named as 4-oxa-PG₁-type compounds. When $Z_1$ is —(CH₂)₃—O—(CH₂)$_g$—, wherein g is as defined above, the compounds so described are named as 3-oxa-PG₁-type compounds.

When $Z_1$ is cis—CH₂—CH=CH—(CH₂)$_g$—CH₂—, wherein g is as defined above, the compounds so described are named as cis-4,5-didehydro-PG₁-type compounds.

For the novel compounds of this invention wherein $Z_1$ is

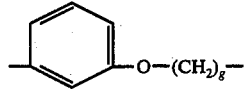

or

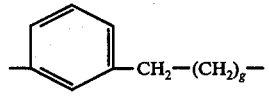

there are described, respectively, 3-oxa-3,7-inter-m-phenylene-4,5,6-trinor or 3,7-inter-m-phenylene-4,5,6-trinor-PG-type compounds.

When $Z_1$ is —C≡C—CH₂—(CH₂)$_g$—CH₂—, wherein g is as defined above, the compounds so described are named as 5,6-didehydro-PG₂-type compounds. When $Z_1$ is —CH₂—C≡C—(CH₂)$_g$—CH₂—, wherein g is as defined above, the compounds so described are named as 4,4,5,5-tetradehydro-PG₁-type compounds.

When $Z_1$ is trans—(CH₂)₂—(CH₂)$_g$—CH=CH—, wherein g is as defined above, the compounds so described are named as trans-2,3-didehydro-PG₁-type compounds.

When g is 2 or 3, the prostaglandin analogs so described are 2a-homo- or 2a,2b-dihomo-PG-type compounds, since in this event the carboxy terminated side chain contains 8 or 9 carbon (or carbon and oxygen) atoms, respectively, in place of the 7 carbon atoms contained in PGF₂α. These additional carbon atoms are considered as though they were inserted between the C-2 and C-3 positions. Accordingly, these additional carbon atoms are referred to as C-2a C-2b, counting from the C-2 to the C-3 position.

The novel prostaglandin analogs of this invention which contain a cis—CH=CH—, —CH₂CH₂— or —C≡C— moiety at the C-13 to C-14 position, are accordingly, referred to as 13-cis-, 13,14-dihydro-, or 13,14-didehydro-PG-type compounds. respectively.

When $R_7$ is —(CH₂)$_m$—CH₃, wherein m is as defined above, the compounds so described are named as 19,20-dinor-, 20-nor-, 20-methyl-, or 2-ethyl-PG-type compounds when m is one, 2, 4, or 5, respectively.

When $R_7$ is

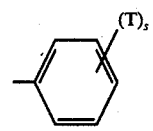

wherein T and s are as defined above, the neither $R_3$ nor $R_4$ is methyl, the compounds so described are named as 16-phenyl-17,18,19,20-tetranor-PG-type compounds, when s is zero. When s is one, 2, or 3, the corresponding compounds are named as 16-(substituted phenyl)-17,18,19,20-tetranor-PG-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl)-18,19,20-trinor-PG-type compounds or 16-methyl-16-phenyl- or 16-(substituted phenyl)-18,19,20-trinor-PG-type compounds, respectively.

When $R_7$ is

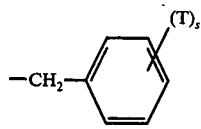

wherein T and s are as defined above, the compounds so described are named as 17-phenyl-18,19,20-trinor-PG-type compounds, when s is zero. When s is one, 2, or 3, the corresponding compounds are named as 17-(substituted phenyl)-18,19,20-trinor-PG-type compounds.

When $R_7$ is

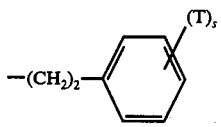

wherein T and s are as defined above, the compounds so described are named as 18-phenyl-19,20-dinor-PG-type compounds, when s is zero. When s is one, 2, or 3, the corresponding compounds are named as 18-(substituted phenyl)-19,20-dinor-PG-type compounds.

When $R_7$ is

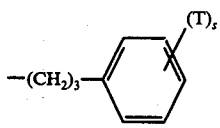

wherein T and s are as defined above, the compounds so described are named as 19-phenyl-20-nor-PG-type compounds, when s is zero. When s is one, 2, or 3, the corresponding compounds are named as 19-(substituted phenyl)-20-nor-PG-type compounds.

When $R_7$ is

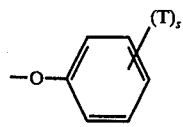

wherein T and s are as defined above, and neither $R_3$ nor $R_4$ is methyl, the compounds so described are named as 16-phenoxy-17,18,19,20-tetranor-PG-type compounds, when s is zero. When s is one, 2, or 3, the corresponding compounds are named as 16-(substituted phenoxy)-17,18,19,20-tetranor-PG-type compounds. When one and only one of $R_3$ and $R_4$ is methyl or both $R_3$ and $R_4$ are methyl, then the corresponding compounds wherein $R_7$ is as defined in this paragraph are named as 16-phenoxy- or 16-(substituted phenoxy)-18,19,20-trinor-PG-type compounds or 16-methyl-16-phenoxy- or 16-(substituted phenoxy)-18,19,20-trinor-PG-type compounds, respectively.

When at least one of $R_3$ and $R_4$ is not hydrogen then (except for the 16-phenyl 16-phenoxy-PG-type compounds discussed above) there are described the 16-methyl- (one and only one of $R_3$ and $R_4$ is methyl), 16,16-dimethyl- ($R_3$ and $R_4$ are both methyl), 16-fluoro- (one and only one of $R_3$ and $R_4$ is fluoro), or 16,16-difluoro-PG-type ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as 15-methyl-PG-type compounds.

With the exception of the 13-cis-PG-type compounds described above, all the above compounds exhibiting a hydroxy in the beta configuration at C-15 are additionally referred to as 15-epi-PG-type compounds. For the 13-cis-PG-type compounds herein, only compounds exhibiting the hydroxy in the alpha configuration at C-15 are referred to as 15-epi-PG-type compounds. The rationale for this system of nomenclature with respect to the natural and epimeric configurations at C-15 is described in U.S. Pat. No. 4,016,184, issued Apr. 5, 1977.

Examples of alkyl of one to 4 carbon atoms, inclusive, are methyl, ethyl, propyl, butyl, and isomeric forms thereof.

Examples of

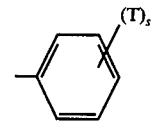

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)ethoxyphenyl, (4- or 5-)chloro-2-methoxyphenyl, and 2,4-dichloro(5- or 6-)methylphenyl.

The novel prostaglandin analogs of the present invention are all useful pharmacological agents, exhibiting high potency as gastrointestinal cytoprotective agents. the gastrointestinal cytoprotective property of the novel prostaglandin analogs herein is evidenced by the ability of these compounds to inhibit the formation of ulcers or other lesions in standard laboratory animals treated with gastrointestinally erosive agents. For a discussion of such laboratory tests, describing the prevention of these gastric lesions by pre-treatment with prostaglandins, see Robert, et al., "Gastric Cytoprotective Property of Prostaglandins", Gastroenterology 72:1121 (1977); and a discussion of such laboratory tests, describing the reduction in intestinal lesions by pretreatment with prostaglandins, see Robert, et al., Gastroenterology 69:1045 (1974), wherein, inter alia, $PGE_2$ is demonstrated to be effective in reducing indomethacin-induced intestinal lesions in the rat.

By virtue of the gastrointestinal cytoprotective property of the novel prostaglandin analogs herein, these compounds are highly useful in the prevention and treatment of inflammatory diseases of the stomach, duodenum, and large and small intestine. For example, the novel prostaglandin analogs herein are employed as gastric cytoprotective agents in the prevention and treatment of gastric erosive diseases, such as gastric ulceration and erosive gastritis. Moreover, the novel prostaglandin analogs herein are useful as intestinal cytoprotective agents in the treatment of numerous intestinal inflammatory diseases, included in which are Crohn's disease, inflammatory bowel disease, infectious enteritis, sprue, and intestinal inflammatory diseases secondary to radiation exposure or allergen exposure. While the novel prostaglandin analogs herein are useful for the present gastrointestinal cytoprotective purposes in a wide variety of mammals, including valuable domestic animals, the principal use of the novel prostaglandin analogs herein is in man.

Accordingly, by this preferred embodiment of the gastric cytoprotective use, the novel prostaglandin analogs herein are used in man for the treatment and prevention of gastric ulcer, duodenal ulcer, gastritis and other gastric inflammatory conditions (e.g., secondary to radiation exposure), by the systemic administration of a dose of a novel prostaglandin analog effective to treat or prevent the development of the disease. In the prophylactic use of these gastric cytoprotective prostaglandins, patients are selected for treatment who exhibit a high susceptibility to the acquisition of a gastric inflammatory disease. Examples of such patients include those with a previous history of gastric or duodenal ulcer; those persons subjected to chronic or acute and stressful environmental conditions, whether of a physical or emotional origin; those manifesting chronic and excessive ethanol consuption (e.g., especially persons diagnosed as alcoholics); and those persons for whom an acute exposure to a cytodestructive dose of ionizing radiation is contemplated. In the latter case, the use of the novel prostaglandin analogs herein in patients receiving therapeutic doses of radiation, for example in the treatment of neoplastic diseases, is particularly contemplated.

When the novel prostaglandin analogs herein are employed as enteric cytoprotective agents, the prophylactic or therapeutic use is undertaken when the animal or patient is in a state of high susceptibility to the development of an intestinal inflammatory disease or the diagnosis of such a disease has been made. Examples of patients exhibiting a high susceptibility to the development of enteric inflammatory diseases include, for example, patients subject to cytodestructive doses of radiation, as indicated above.

With regard to the systemic administration of the novel compounds of the present invention, any convenient systemic route is employed, although oral administration is the highly preferred route. While the oral route is preferred, for patients where this route of administration is inconvenient or unacceptable, other routes such as via a nasogastric tube or via suppositories and enemas are likewise preferred. For a description of the various methods of formulation and routes of administration by which the novel prostaglandin analogs herein are employed, see United States Patent 3,903,297.

The dosage regimen and duration of treatment for the novel prostaglandin analogs herein will depend upon a wide variety of factors, including the type, age, weight, sex, medication condition of the animal or patient being treated and the nature and severity of the gastric or enteric inflammatory disease to be treated or prevented. For example, oral doses between 25 mg/kg/day and 0.5 µg/kg/day will ordinarily be gastrointestinally cytoprotective. Once a minimum effective dose for the particular novel prostaglandin analog herein is determined for a particular animal or patient, that animal or patient is thereafter advantageously provided with a daily dosage schedule which will provide a substantially uniform level of the novel cytoprotective analog throughout the day.

Moreover, treatment with the novel prostaglandin analog herein should be continued therapeutically until the gastrointestinal inflammatory disease has been successfully arrested, and thereafter a prophylactic regimen with the prostaglandin analog should be maintained until susceptibility to the recurrence of the disease is no longer high. Thus, in the case of an acute exposure to a noxious atent, treatment for several days to several weeks will ordinarily be sufficient. However, in cases where a patient, for example, has a history of multiple recurrences of gastric or duodenal ucler, prophylactic treatment may be maintained indefinitely, based upon the continued tolerance to the drug.

CHART A

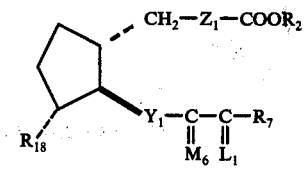

XXI

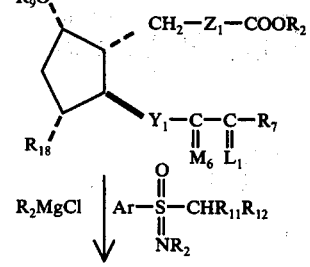

XXII

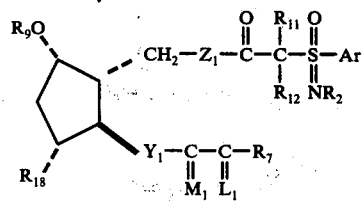

XXIII

CHART A
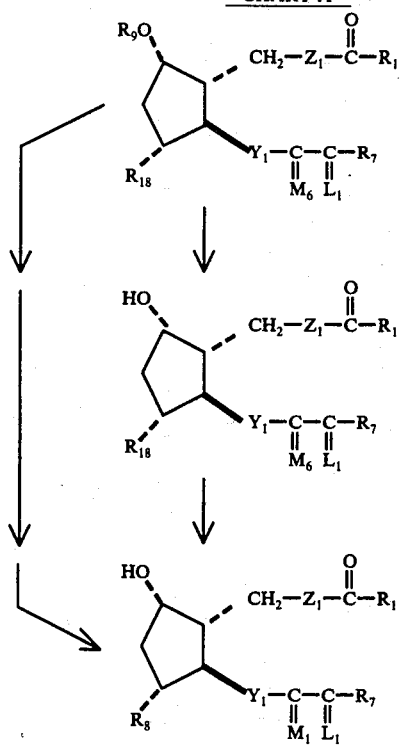
XXIV
XXV
XXVI
CHART B
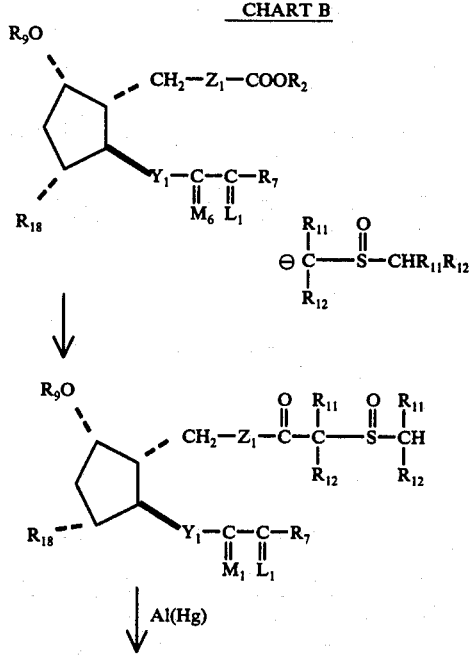
XXXI
XXXII
↓ Al(Hg)
XXXIII
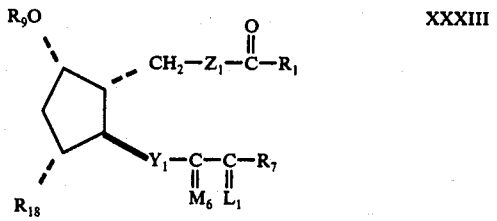
CHART C
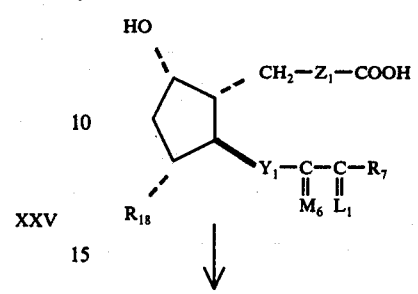
XLI
XLII
XLIII
XLIV
↓ R₁Mg Br
XLV
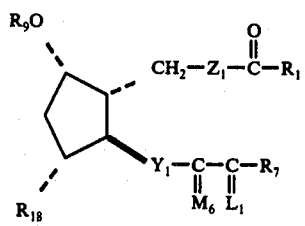

CHART D
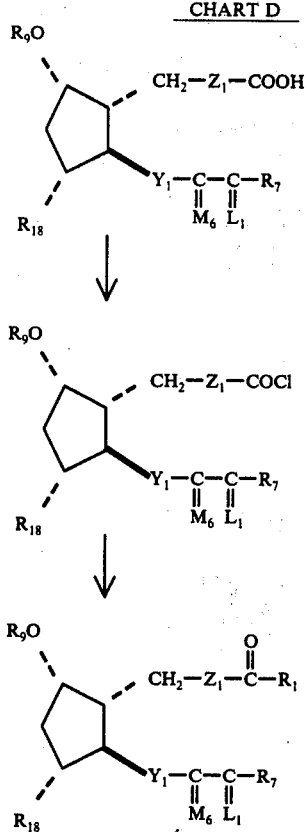
CHART E
CHART F
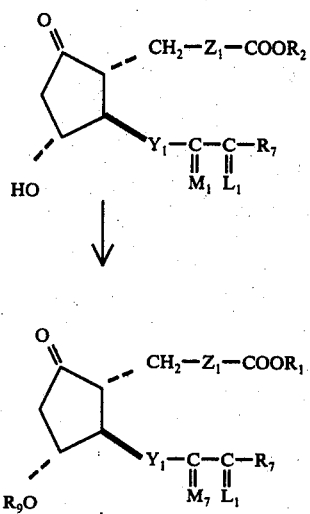
LI
LII
LIII
LXI
LXII
LXIII
LXXI
LXXII
LXXIII
LXXIV
CHART G
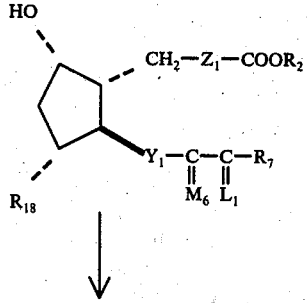
LXXXI -continued
CHART G

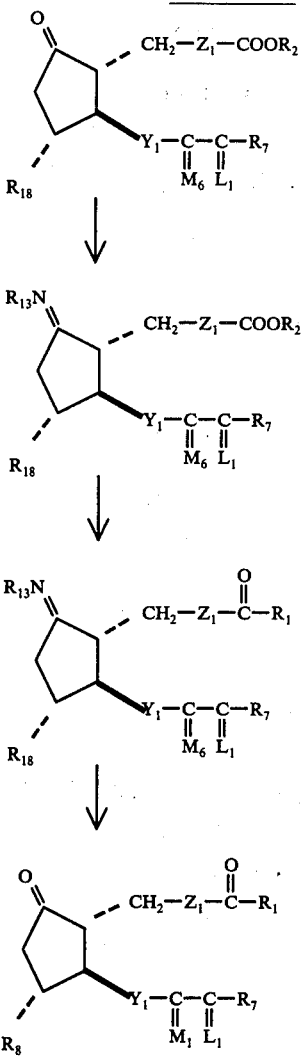

LXXXII

LXXXIII

LXXXIV

LXXXV

The charts herein provide exemplary methods by which the novel 2-decarboxy-2-alkylcarbonyl-PG-type compounds of the present invention are prepared. With respect to the charts, $R_{18}$ is hydrogen or protective group - derivatized hydroxyl, wherein said protective group is selected from among acetal-type ethers (e.g., tetrahydrofuran, tetrahydropyran, and 1-epoxyethyl) and stable silyl groups such as t-butyldimethylsilyl. For examples of protective groups apposite to the instant purposes see U.S. Pat. No. 4,016,184. $R_8$ is hydroxy of hydrogen; $R_2$ is alkyl of one to 4 carbon atoms, inclusive, preferably being methyl or ethyl; $R_{11}$ and $R_{12}$ are such that moiety $-CHR_{11}R_{12}$ is primary or secondary alkyl of one to 4 carbon atoms, inclusive; $R_9$ is trialkylsilyl of the formula $-S_i(G_1)_3$, wherein $G_1$ is alkyl of one to 4 carbon atoms, inclusive, the various $G_1$'s being the same or different and preferably all being methyl; and $R_{13}$ is $-OH$, $-NCONH_2$, $-NCSNH_2$, or $-NOR_2$. $M_6$ and $M_7$ are hydroxyl derivatized forms of $M_1$ wherein the hydroxyl group is replaced by an ether-type derivative. For $M_6$, the derivative is a protecting group as in $R_{18}$, while for $M_7$ the derivative is a silyl group as defined by $R_9$.

Aryl is an aromatic carbocyclic radical, preferably being phenyl. Hal is halogen, preferably being chloro or bromo.

$R_1$, $R_7$, $M_1$, $L_1$, and $Z_1$ are as defined above.

Chart A provides a method whereby the formula XXI PGFα- or 11-deoxy-PGFα-type 11,15-bis ether of 15-ether is transformed to the formula XXVI 2-decarboxy-2-alkylcarbonyl-PGFα- or 11-deoxy-PGFα-type compounds of the present invention.

The formula XXI compound is known in the art or readily prepared by methods known in the art. See for example the above references describing the preparation of PGFα- and 11-deoxy-PGFα-type compounds exhibiting the various C-8 and C-12 side chain modifications as evidenced by formula XXI.

The formula XXII compound is prepared from the formula XXI compound by silyl protection of the C-9 hydroxyl.

Methods for such monosilylation of PG-type products with the trialkylsilyl groups of $R_9$ are described in U.S. Pat. No. 4,016,184.

The formula XXII compound is thereafter transformed to the formula XXIII sulfoximine ester by reaction with an S-aryl-N-alkyl-S-alkylsulfoximine in the presence of a lower alkyl Grignard reagent (e.g., an alkyl magnesium chloride). The reaction ordinarily proceeds to completion in several minutes to an hour at low temperature, i.e., less than or equal to 0° C. For example, the reaction conveniently employs S-phenyl-N,S, dimethylsulfoximine with methyl magnesium chloride in a tetrahydrofuran solvent at 0° to −78° C. when preparing the formula XXIII compound wherein $R_{11}$ and $R_{12}$ are both hydrogen.

Thereafter, the formula XXIV ketone is prepared from the formula XXIII compound by an aluminum amalgam reduction. Conventional methods for the preparation of aluminum amalgams are employed and the reaction, being slightly exothermic, is ordinarily completed at about ambient temperature in about one hr after treatment of the formula XXIII compound with the amalgam. For a detailed description of the preparation of the aluminum amalgam and its instant reductive use, see the description in U.S. Pat. No. 3,950,363, wherein aluminum amalgams are employed in the preparation of 9-deoxy-9-methylene-PGF-type compounds.

Thereafter the formula XXV compound is prepared from the formula XXIV compound by selective hydrolysis of the C-9 silyl group. For example, the tri(primary alkyl) silyl group according to $R_9$ is hydrolyzed in the presence of citric acid and aqueous methanol at between 0° and 25° C., reaction conditions under which the acetal type protective groups according to $R_{18}$ or dialkyl-(tertiary alkyl) silyl groups according to $R_{18}$ are not so hydrolyzed. The formula XXV 2-carboxy-2-alkylcarbonyl-PGFα- or 11-deoxy-PGFα-type, 11,15-bis ether or 15-ether is then readily and efficiently oxidized to the corresponding 2-decarboxy-2-alkylcarbonyl-PGE- or 11-deoxy-PGE-type, 11,15-bis ether or 15-bis ether, in accordance with methods known in the art. Moreover, hydrolysis of these 2-decaroboxy-2-alkylcarbonyl-PGE- or 11-deoxy-PGE-type 11,15-bis ethers or 15 ethers is accomplished by methods hereinafter described for the preparation of the formula XXVI compounds, yielding the corresponding 2-decarboxy-2-alkylcarbonyl-PGE- or 11-deoxy-PGE-type products.

These 2-decarboxy-2-alkylcarbonyl-PGE- or 11-deoxy-PGE-type products are thereafter transformed to corresponding 2-decarboxy-2-alkylcarbonyl-PGAor PGB-type products by acidic or basic dehydration, respectively, in accordance with methods known in the art. Further the 2-decarboxy-2-alkylcarbonyl-PGE- or 11-deoxy-PGE-type products are selectively reduced to the corresponding 2-decarboxy-2-alkylcarbonyl-PGFβ- or 11-deoxy-PGFβ-type products, in accordance with methods known in the art.

Finally, the 2-decarboxy-2-alkylcarbonyl-PGE-type 11,15-bis ethers are transformed to corresponding 2-decarboxy-2-alkylcarbonyl-9-deoxy-9-methylene-PGF-type 11,15-bis ethers employing methods described in U.S. Pat. No. 3,950,363. Accordingly, these 2-decarboxy-2-alkylcarbonyl-9-deoxy-9-methylene-PGF-type products are prepared by a sulfoximine addition, as described in the preparation of the formula XXIII compound from the formula XXII compound; and hydrolysis of the ether groups, as described in the preparation of the formula XXVI compound hereinbelow; and an aluminum amalgam reduction, as described in the preparation of the formula XXIV compound from the formula XXIII compound.

The formula XXVI compound is prepared from the formula XXV compound by hydrolysis of the dialkyl (tertiary alkyl) silyl or acetyl-type protective groups, employing methods known in the art. For example mixtures of acetic acid, water, and tetrahydrofuran at 40° C. are conveniently employed. See in particular the methods for hydrolysis described in U.S. Pat. No. 4,016,184.

The formula XXVI compound represents a 2-decarboxy-2-alkylcarbonyl-PGF -or 11-deoxy-PGF -type product of the present invention. Such formula XXVI products are transformed to the corresponding 2-decarboxy-2-alkylcarbonyl-PGD-9β-PGD- or 9-deoxy-9,10-didehydro-PGD-type products according to methods known in the art. For a description of such methodology see U.S. Pat. No. 4,016,184.

For each of the various 2-decarboxy-2-alkylcarbonyl-PG-type products exhibiting a PGFα, PGFβ, PGE, 11-deoxy-PGFα, 11-deoxy-PGFβ, 11-deoxy-PGE, PGA,9-deoxy-9-methylene-PGF, PGD, 9β-PGD, or 9-deoxy-9,10-didehydro-PGD parent structure, corresponding 8β,12α-PG-type products are prepared by employing the 8β,12α isomer of the formula XXII compound. Such 8β,12α-PGFα- or 11-deoxy-PGFα-type reactants according to formula XXI are known in the art or prepared by methods known in the art. Most particularly, methodology for the preparation of these stereoisomers is described in U.S. Pat. No. 3,979,438. Accordingly, there are prepared by procedures described hereinabove from these 8β,12α-PGFα- or 11-deoxy-PGFα-reactants of formula XXII 2-decarboxy-2-alkylcarbonyl-8β,12α-PGFα- PGFβ-, PGE-, 11-deoxy-PGFα-, 11-deoxy-PGFβ-, 11-deoxy-PGE-, PGA-, 9-deoxy-9-methylene-PGF-, PGD-, 9β-PGD-, or 9-deoxy-9,10-didehydro-PGD-type products.

Accordingly, there are prepared from the formula XXI - formula XXVI compounds of Chart A, or the 8,12-PG-type stereoisomers thereof 2-decarboxy-2-(primary alkyl)carbonyl- or 2-(secondary alkyl)carbonyl-PG-type products of the present invention.

Chart B provides a method analagous to that described in Chart A whereby the formula XXXI compound of Chart B (the formula XXII compound of Chart A) is transformed to a formula XXXIII 2-decarboxy-2-(primary or secondary)alkyl-PGFα- or 11-deoxy-PGFα-type intermediate according to formula XXXIII (the formula XXIV compound of Chart A). In accordance with the method of Chart B, the formula XXXI compound is reacted with an anion generated from a symmetrical bis(primary or secondary alkyl)sulfoxide to yield the formula XXXII sulfoxide ester. The bisalkylsulfoxide anion is generated from a symmetrical compound of the formula $CHR_{11}R_{12}SOCHR_{11}R_{12}$ by reaction with a strong base. Appropriate bases include potassium t-butoxide and sodium hydride. The general methodology for preparing sulfoxide esters is known in the art. See for example Corey, E. J., et al., JACS 86:1639 (1964).

The formula XXXII compound is then reduced, employing an aluminum amalgam, to yield the formula XXXIII 2-decarboxy-2-(primary or secondary alkyl)-carbonyl-PGFα- or 11-deoxy-PGFα- intermediate. Suitable reaction conditions are known in the art and are for example described by Corey, E. J., et al. JACS 86:1639 (1964). These formula XXXIII compounds of Chart B are then employed in the preparation in various 2-decarboxy-2-(primary or secondary alkyl)carbonyl-PG-type products of the present invention by methods described in Chart A from the preparation of such products from the formula XXIV compound.

Chart C provides yet a third method whereby 2-decarboxy-2-alkylcarbonyl-PGFα- or 11-deoxy-PGFα-type intermediates are prepared, which intermediates can thereafter be transformed to the various 2-decarboxy-2-alkylcarbonyl-PG-type products of the present invention. In distinction to the methods described in Chart A and B, the method described in Chart C provides for the preparation of intermediates which are ultimately transformed (by methods described above) to 2-decarboxy-2-(2-tertiary alkyl)carbonyl-PG-type products of the present invention.

The method of Chart C provides for the transformation of the formula XLI carboxylic acid, as known in the art or as is readily prepared by methods known in the art, to the formula XLV 2-decarboxy-2-(primary, secondary, or tertiary alkyl)carbonyl-PGFα- or 11-deoxy-PGFα-type intermediates.

In accordance with the method of Chart C, the formula XLI carboxylic acid is transformed to the formula XLII silyl ether - silyl ester by silylation methods described above for the preparation of the formula XXII compound of Chart A.

The formula XLIII compound is then prepared from the formula XLII compound by hydrolysis of the silyl esters. The hydrolysis of the esters proceed efficiently in an aqueous medium, especially aqueous media containing sufficient amounts of organic solvent (e.g., ethanol) to assure solubility of the formula XLII reactant. Having prepared the formula XLIII acid, the 2-pyridyl ester thereof is prepared by reacting the acid with 2,2'-dipyridyl disulfide in the presence of triphenylphosphine. Appropriate reaction conditions for such an esterification are known in the art. See for example Corey, E. J., et al., JACS 97:653 (1975).

Thereafter, an alkyl Grignard reagent is employed in the transformation of the formula XLIV compound to the corresponding formula XLV 2-decarboxy-2-(alkyl-carbonyl-PGFα- or 11-deoxy-PGFα-type intermediate. This ketonization reaction is known in the art, being described by Mukaiyama, T., et al., JACS 95:4763 (1973).

Chart D provides yet a fourth method whereby the formula LIV 2-decarboxy-2-alkylcarbonyl-PGFα- or 11-deoxy-PGFα-type intermediate is prepared. By the method of Chart D, the formula LI compound, prepared as the formula XLIII compound in Chart A, is firstly transformed to the formula LII acid chloride. Methods known in the art for the generation of such acid chlorides are employed. For example, by one convenient method oxalyl chloride is employed. The formula LII acid chloride thusly prepared is then transformed to the formula LIII 2-decarboxy-2-alkylcarbonyl-PGFα- or 11-deoxy-PGFα-type intermediate by reaction with a dialkyl copper (I) lithium reagent corresponding to the formula III 2-decarboxy-2-alkylcarbonyl-PGFα- or 11-deoxy-PGFα-type intermediate to be prepared. The copper lithium reagent is generated by reaction of, for example, cuperous iodide with the desired alkyllithium compound and thereafter combining the reagent thusly prepared with the formula LII compound. The reaction is appropriately undertaken at low temperature ($-20°$ to $-78°$ C.) and is ordinarily complete within several minutes. For a description of the general reaction conditions employed herein, see Posner, G., et al. Tetrahedron Lett. 4676 (1970).

Chart E provides yet a fifth method whereby the formula LXIII 2-decarboxy-2-alkylcarbonyl-PGFα- or 11-deoxy-PGFα-type intermediate is prepared. By the method of Chart E, this intermediate is prepared from the formula LXII acid chloride, prepared as the formula LII compound of Chart D. The acid chloride is then reacted with $Na_2Fe(CO)_4$ to yield the formula LII ester, which ester is thereafter reacted with an alkyl halide corresponding to the formula LXIII 2-decarboxy-2-alkylcarbonyl-PGFα- or 11-deoxy-PGFα-type intermediate to be prepared. The method for preparing ketones of the present type is known in the art. See for example Collman, J. P., et al., JACS 94:1788 (1972).

Chart F provides an especially convenient method whereby the preparation of the formula LXXIV 2-decarboxy-2-methylcarbonyl-9-deoxy-9-methylene-PGF-type products are prepared. Methods analagous to those in Chart F for preparing the carboxylic acids corresponding to the formula LXXIV ketones are described in U.S. Pat. Nos. 4,012,467 and 4,060,343, where the instant formula LXXIV ketones represent uncharacterized and unappreciated reaction side products of the preparation of the 9-deoxy-9-methylene-PGF-type compounds described therein. Accordingly, the silylation of the formula LXXXI compound to the formula LXXXII compound proceeds as is described in U.S. Pat. No. 4,021,467; and thereafter the silylated formula LXXXII compound is reacted with an S methyl-S-aryl-N-alkyl-sulfoxamine reagent in the presence of an alkyl Grignard reagent in a manner described in Chart A for the preparation of the formula XXIII compound therein. While substantial yields of the formula LXXII product can be obtained by allowing the reaction to proceed at from 0° to $-78°$ C. by employing a single equivalent of the sulfoxamine reagent, the preferred reaction conditions for the preparation of the formula LXXIII compound are the employment of three to four equivalents of the sulfoxamine reagent with reaction proceeding at 0° C. to ambient temperature. While reaction conditions may be maintained for as short a period as 2 hrs, preferred reaction times are 4–6 hrs.

Thereafter the formula LXXIV product is prepared in the manner described above for the preparation of the formula XXVI compound of Chart A, e.g., the protection followed by aluminum amalgam reduction.

Chart G provides a method whereby the cyclopentanone products of formula LXXXV are prepared from the formula LXXXI PGFα- or 11-deoxy-PGFα-, 11,15-bis ethers or 15-ethers.

In accordance with the method of Chart D, the formula LXXXI compound is first oxidized to the formula LXXXII PGE- or 11-deoxy-PGE-, 11,15-bis ether or 15-ether by methods known in the art. For example, known reducing agents for transforming PGF-type compounds to the corresponding PGE derivatives such as the Collins reagent or the Jones reagent are employed. Thereafter, the cyclopentanone ring of the formula LXXXII compound is derivatized to the formula LXXXIII oxime, semicarbazone, thiosemicarbazone, or alkoxyoxime. The preparation of such derivatives of the formula LXXXII compound is readily accomplished by methods known in the art. See for example U.S. Pat. No. 3,723,528, describing the conversion of similar cyclopentanone compounds to corresponding nitrogen-containing derivatives.

The formula LXXXIII compound is then transformed to the formula LXXXIV 2-decarboxy-2-alkylcarbonyl derivative by any one of the methods described in Charts A-E above. Preferred among such methods described above for the present purpose is that described in Charts A and C.

Finally, the formula LXXXIV compound is hydrolyzed to the formula LXXXV product, employing, again, methods described in U.S. Pat. No. 3,723,528 for transforming the oxime, semicarbazone, thiosemicarbazone, or alkoxyoxime derivatives to corresponding cyclopentanones and other hydrolytic methods (e.g., for the removal of protective groups) as described above.

By a variation of the method described in Chart G, the various other novel prostaglandin analogs herein exhibiting a cyclopentanone or cyclopentanone ring are likewise prepared by the methods described in Chart G by substituting the corresponding carboxylic acids thereof in place of the formula LXXXII compound. For example, the 2-decarboxy-2-alkylcarbonyl-PGA-type compounds of the present invention are prepared in accordance with the method of Chart G by subjecting the corresponding PGA-type, alkyl ester, 15-ether to the sequence of reaction steps employed in the transformation of the formula LXXXII compound to the formula LXXXV products.

Further, as indicated above, when 8β,12α-PG-type products are desired, the respective procedures of Charts A-G are followed, with the exception that, corresponding 8β,12α-PG-type starting materials are employed. Such starting materials are known in the art or readily prepared by methods known in the art and indicated above.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M Hamberg and B. Samuelsson, J. Biol. Chem. 241, 257 (1955).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-John or Thomas-Hoover melting point apparatus.

THF refers to tetrahydrofuran.

Specific Rotations, ($\alpha$), are determined for solutions of a compound in the specified solvent at ambient temperature with a Perkin-Elmer Model 141 Automatic Polarimeter.

EXAMPLE 1 —
2-Decarboxy-2-methylcarbonyl-16,16-dimethyl-9-deoxy-9-methylene-PGF$_2$ (Formula LXXIV: $Z_1$ is cis-CH=CH-(CH$_2$)$_3$-, $Y_1$ is trans-CH=CH-, $R_5$ of the $M_1$ moiety is hydrogen, $R_3$ and $R_4$ of the $L_1$ moiety are both methyl, and $R_7$ is n-butyl).

Refer to Chart F.

A. A solution of 8.78 g of S-methyl-S-phenyl-N-methylsulfoximine in 150 ml of tetrahydrofuran was cooled to 0° C. and treated dropwise over 10 min with 16.9 ml of 2.9 M methylmagnesium chloride in tetrahydrofuran. After 15 min at 0° C. the resulting sulfoximine ion-solution was cooled to −78° C. and added dropwise over 15 min to a stirred solution of 13.8 g of 16,16-dimethyl-PGE$_2$, methyl ester, 11,15-bis(tetrahydropyranyl ether) in 70 ml of tetrahydrofuran at −78° C. The resulting solution is then stirred at −78° C. for 2.5 hrs and thereafter treated with 20 ml of saturated aqueous ammonium chloride. After an additional 10 min, the resulting mixture is then poured into a mixture of ice, aqueous ammonium chloride, and diethyl ether. Extracting with diethyl ether, washing with brine, drying over sodium sulfate, and concentrating under reduced pressure yields a residue containing the formula LXXIII sulfoxamine ester.

B. Aluminum metal (20 g of 20 mesh) is washed with diethyl ether and methanol. The metal is then combined with 20 g of mercuric chloride in 150 ml of water. The resulting suspension is then swirled until appreciable hydrogen evolution is noted. The solution is then decanted and the resulting aluminum amalgam then washed with methanol and diethyl ether, rendering is suitable for immediate use.

C. The reaction product from Part A above is dissolved in 650 ml of tetrahydrofuran and diluted with water in acetic acid (100 ml each). Resulting mixture is then treated with about 28 g of the aluminum amalgam prepared in Part B, with the resulting suspension being stirred in a cool (15°-20° C.) water bath for 1 hr. Thereafter, 20 g of diatomaceous earth is added and the resulting mixture stirred an additional 10 min. The mixture is then filtered through a pad of diatomaceous earth and the filter solids washed with tetrahydrofuran. The filtrate is then concentrated under reduced pressure, thereby removing the tetrahydrofuran; diluted with brine (500 ml); extracted with ethyl acetate and hexane (1:1, 1400 ml); and backwashed with brine (1600 ml) and 0.5 M aqueous sodium phosphate (dibasic, ph 9), until the aqueous washes were at pH 8–9. The ethereal extracts are then washed with brine, dried over magnesium sulfate, and concentrated under reduced pressure to yield a 20.1 g mixture containing crude 2-decarboxy-2-methylcarbonyl-16,16-dimethyl-9-deoxy-9-methylene-PGF$_2$, 11,15-bis(tetrahydropyranyl ether).

The crude product from Part C is then dissolved in a mixture of 50 ml of tetrahydrofuran, 100 ml of water, and 200 ml of acetic acid; stirred at 25° C. for 4.5 hrs; partially concentrated under reduced pressure at 40° C. (for removal of the tetrahydrofuran); diluted with brine (500 ml); and extracted with ethyl acetate and hexane (1:1; 1300 ml). The extracts are then washed with 0.5 M aqueous sodium phospate (dibasic, pH 9) under basic extracts are obtained, and brine (400 ml). Drying over magnesium sulfate and concentrating under reduced pressure yields a 12 g mixture containing crude title product. Chromatography on 1.5 kg of silica gel packed with 20% ethyl acetate and hexane and eluted with ethyl acetate and hexane (1:4, 5 l; 3:7, 5 l; 2:3; 15 l [fractions 1–40]; and 3:2, 5 l [fractions 41–52]). Fractions 11–23 yield 4.7 g of 9-deoxy-9-methylene-16,16-dimethyl-PGF$_2\alpha$. methyl ester, while fractions 27–40 yield 940 mg (9%) of pure 2-decarboxy-2-methylcarbonyl-16,16-dimethyl-9-deoxy-9-methylene-PGF$_2$, the title product. Infrared absorptions are observed at 3400, 1710, 1650, 1355, 1155, 1070, 1020, 1000, 970, and 880 cm$^{-1}$. NMR absorptions are observed at 5.65-5.20, 4.9, 3.90-3.50, 2.13, 0.82, and 0.87 $\delta$. The mass spectrum of the trimethylsilyl derivative exhibits a weak molecular ion at 520; a demethylated high resolution peak at 505.3525; other peaks at 421, 331, and 241.

Following the procedure of Example 1, there are prepared from each of the formula LXXII PGE-type compounds the corresponding formula LXXIV 2-decarboxy-2-methylcarbonyl-9-deoxy-9-methylene-PGF-type products of the present invention.

EXAMPLE 2 —
2-Decarboxy-2-methylcarbonyl-cis-4,5-didehydro-16,16-dimethyl-9-deoxy-9-methylene-PGF$_2$ (Formula LXXIV: $Z_1$ is cis-CH$_2$-CH=CH(CH$_2$)$_2$-, $Y_1$ is trans-CH=CH-, $R_5$ of the $M_1$ moiety is hydrogen, $R_3$ and $R_4$ of the $L_1$ moiety are both methyl, and $R_7$ is n-butyl)

Refer to Chart F.

A. To a solution of 6.0 g of cis-4,5-didehydro-16,16-dimethyl-9-deoxy-9-methylene-PGF$_1$, methyl ester in 180 ml of tetrahydrofuran is added 45 ml of hexamethyldisilazane and 18 ml of chlorotrimethylsilane. The resulting mixture is then stirred for 2 days at 25° C. under a nitrogen atmosphere. Thereafter the reaction mixture is concentrated under reduced pressure, removing the hexamethyldisilazane. The residue is then dissolved in xylene; filtered through diatomaceous earth, thereby removing ammonium chloride; concentrated under reduced pressure at 50° C.; and finally twice dissolved in zylane (50 ml) and concentrated under reduced pressure to a residue. The residue, consisting of about 70% formula LXXII compound, cis-4,5-didehydro-16,16-dimethyl-9-deoxy-9-methylene-PGF$_1$, 11,15-bis(trimethylsilyl ether), and 30% cis-4,5-didehydro-16,16-dimethyl-9-deoxy-9-methylene-PGF, 11-(trimethylsilyl ether), is used in Part B without further purification.

B. Following the procedure of Example 1, Part A. 5.28 g of S-methyl-S-phenyl-N-methyl-sulfoxamine and the reaction product of Part A yield the formula LXXIII compound corresponding to the instant title product.

C. Following the procedure of Example 1, Part B, aluminum amalgam (13 g) and the crude formula LXXIII reaction product of Part B are reacted to yield 2.3 g of cis-4,5-didehydro-16,16-dimethyl-PGF$_1$, methyl ester and 930 mg of pure title product, 2-decarboxy-2-methylcarbonyl-cis-4,5-didehydro-16,16-dimethyl-9-deoxy-9-methylene-PGF$_1$. There is further obtained a 215 mg mixture of the methyl ester and title product. For the title product, infrared absorptions are observed at 3500, 3100, 1720, 1660, 1240, 1160, 1080, 1050, 975, 890, and 735 cm$^{-1}$. NMR absorptions are observed at 5.75-5.15, 5.0-4.75, 3.95-3.55, 2.65, 2.10, 0.87, and 0.84 $\delta$. The mass spectrum for the trimethylsilyl derivative exhibits a weak molecular ion at 520; a demethylated high resolution peak at 505.3519; and other peaks at 463, 421, 331, 243, and 99.

EXAMPLE 3 —
2-Decarboxy-2-methylcarbonyl-17-phenyl-18,19,20-trinor-9-deoxy-9-methylene-PGF$_2$ (Formula LXXIV: Z$_1$ is cis-CH=CH—(CH$_2$)$_3$—, Y$_1$ is trans-CH=CH-, R$_5$ of the M$_1$ moiety and R$_3$ and R$_4$ of the L$_2$ moiety are all hydrogen, and R$_7$ is benzyl).

Refer to Chart F.

Following the procedure of Example 2, Part A, 1.7 g of 17-phenyl-18,19,20-trinor-PGE$_2$, methyl ester and 1.5 ml of chlorotrimethylsilane are reacted to yield 2.1 g of crude formula LXXII compound, 17-phenyl-18,19,20-trinor-PGE$_2$, methyl ester, 11,15-bis(trimethylsilyl ether). Silica gel TLC Rf is 0.5 in ethyl acetate and hexane (1:4).

Following the procedure of Example 2, Part B, 2.0 g of S-methyl-S-phenyl-N-methyl-sulfoxamine and the crude bis(trimethylsilyl ether) obtained above are reacted to yield a crude mixture containing the formula LXXIII compound corresponding to the title product.

Following the procedure of Example 2, Part C, the crude formula LXXIII product obtained above is transformed to the corresponding title product, 215 mg of 2-decarboxy-2-methylcarbonyl-17-phenyl-18,19,20-trinor-9-deoxy-9-methylene-PGF$_2$, and 482 mg of the corresponding methyl ester (9-deoxy-9-methylene-17-phenyl-18,19,20-trinor-PGF$_2\alpha$, methyl ester). Infrared absorptions are observed at 3400, 3100, 1720, 1660, 1610, 1360, 1160, 1070, 970, 885, 750, and 700 cm$^{-1}$.

NMR absorptions are observed at 7.35-7.05, 5.70-5.25, 5.05-4.80, 4.3-3.4, and 2.05 $\delta$. The mass spectrum for the trimethylsilyl derivative exhibits a high resolution molecular ion at 526.3290 and other peaks at 511, 436, 421, 401, 331, 311, 207, and 91.

EXAMPLE 4 —
2-Decarboxy-2-methylcarbonyl-9-deoxy-9-methylene-PGF$_2$ (Formula LXXIV: Z$_1$ is cis-CH=CH—(CH$_2$)$_3$—, Y$_1$ is trans-CH=CH—, R$_3$ and R$_4$ of the L$_1$ moiety and R$_5$ of the M$_1$ moiety are all hydrogen, and R$_7$ is n-butyl).

Refer to Chart F.

PGE$_2$, methyl ester, 11,15-bis(trimethylsilyl ether), 25 g, and S-methyl-S-phenyl-N-methyl-sulfoxamine (13.25 g) are reacted according to the procedure of Example 2, Part B, yielding a crude product which is reduced with 35 g of aluminum amalgam according to the procedure of Example 2, Part C. There is obtained in this manner 10.84 g of pure 9-deoxy-9-methylene-PGF$_2$, methyl ester and 1.42 g of pure title product, 2-decarboxy-2-methylcarbonyl-9-deoxy-9-methylene-PGF$_2$. Infrared absorptions are observed at 3400, 3100, 1720, 1660, 1360, 1160, 1075, 1020, 970, and 885 cm$^{-1}$. NMR absorptions are observed at 5.65-5.25, 5.04-4.80, 4.3-3.50, and 2.21 $\delta$. The mass spectrum for the trimethylsilyl derivative exhibits a high resolution molecular ion at 492.3479 and other peaks at 477, 421, 402, 367, 331, 312, 277, 243, 199, and 173.

Following the procedure of the Examples 1-4, but employing the appropriate PGE$_2$-type or 8$\beta$,12$\alpha$-PGE$_2$-type starting material, there are prepared
2-decarboxy-2-methylcarbonyl-9-deoxy-9-methylene-PGF$_2$- type compounds; or
2-decarboxy-2-methylcarbonyl-9-deoxy-9-methylene-8$\beta$,12$\alpha$-PGF$_2$- type compounds;
which exhibit the following side chain characteristics:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-trinor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-13,14-didehydro-;
16,16-Dimethyl-16-phenoxy-18,19,20-trinor-;
13,14-Didehydro-;
15-Methyl-13,14-didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;

16-Methyl-17-phenyl-18,19,2+-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-fluorophenyl)-17,18,19,20-tetranor-13,14-didehydro-;
16-(p-fluorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenyl)-17,18,19,20-tetranor-13,14-didehydro-;
16-(p-fluorophenyl)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
15-Methyl-13,14-dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-didehydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
15-epi-13-cis-;
15-Methyl-15-epi-13-cis-;
16-Methyl-15-epi-13-cis-;
16,16-Dimethyl-15-epi-13-cis-;
16-Fluoro-15-epi-13-cis-;
16,16-Difluoro-15-epi-13-cis-;
17-Phenyl-18,19,20-trinor-15-epi-13-cis-;
17-(m-trifluoromethylphenyl)-18,19,20-trinor-15-epi-13-cis-;
17-(m-chlorophenyl)-18,19,20-trinor-15-epi-13-cis-;
17-(p-fluorophenyl)-18,19,20-trinor-15-epi-13-cis-;
16-Methyl-17-phenyl-18,19,20-trinor-15-epi-13-cis-;
16,16-Dimethyl-17-phenyl-18,19,20-trinor-15-epi-13-cis-;
16-Fluoro-17-phenyl-18,19,20-trinor-15-epi-13-cis-;
16,16-Difluoro-17-phenyl-18,19,20-trinor-15-epi-13-cis-;
16-Phenyl-17,18,19,20-tetranor-15-epi-13-cis-;
16-(m-trifluoromethylphenyl)-17,18,19,20-tetranor-15-epi-13-cis-;
16-(m-chlorophenyl)-17,18,19,20-tetranor-15-epi-13-cis-;
16-(p-fluorophenyl)-17,18,19,20-tetranor-15-epi-13-cis-;
16-Phenyl-18,19,20-trinor-15-epi-13-cis-;
16-Methyl-16-phenyl-18,19,20-trinor-15-epi-13-cis-;
16-Phenoxy-17,18,19,20-tetranor-16-epi-13-cis-;
16-(m-trifluoromethylphenoxy-17,18,19,20-tetranor-15-epi-13-cis-;
16-(m-chlorophenoxy)-17,18,19,20-tetranor-15-epi-13-cis-;
16-(p-chlorophenoxy)-17,18,19,20-tetranor-15-epi-13-cis-;
16-Phenoxy-18,19,20-trinor-15-epi-13-cis-;
16-Methyl-16-phenoxy-18,19,20-trinor-15-epi-13-cis-;
2a,2b-Dihomo-;
2a,2b-Dihomo-16-methyl-;
2a,2b-Dihomo-16,16-dimethyl-;
2a,2b-Dihomo-16-fluoro-;
2a,2b-Dihomo-16,16-difluoro-;
2a,2b-Dihomo-17-phenyl-18,19,20-trinor-;
2a,2b-Dihomo-17-(m-trifluoromethylphenyl)-18,19,20-trinor-;
2a,2b-Dihomo-17-(m-chlorophenyl)-18,19,20-trinor-;
2a,2b-Dihomo-17-(p-fluorophenyl)-18,19,20-trinor-;
2a,2b-Dihomo-16-methyl-17-phenyl-18,19,20-trinor-;
2a,2b-Dihomo-16,16-dimethyl-17-phenyl-18,19,20-trinor-;
2a,2b-Dihomo-16-fluoro-17-phenyl-18,19,20-trinor-;
2a,2b-Dihomo-16,16-difluoro-17-phenyl-18,19,20-trinor-;
2a,2b-Dihomo-16-phenyl-17,18,19,20-tetranor-;
2a,2b-Dihomo-16-(m-trifluoromethylphenyl)-17,18,19,20-tetranor-;
2a,2b-Dihomo-16-(m-chlorophenyl)-17,18,19,20-tetranor-;
2a,2b-Dihomo-16-(p-fluorophenyl)-17,18,19,20-tetranor-;
2a,2b-Dihomo-16-phenyl-18,19,20-trinor-;
2a,2b-Dihomo-16-methyl-16-phenyl-18,19,20-trinor-;
2a,2b-Dihomo-16-phenoxy-17,18,19,20-tetranor-;
2a,2b-Dihomo-16-(m-trifluoromethylphenoxy)-17,18,19,20-tetranor-;
2a,2b-Dihomo-16-(m-chlorophenoxy)-17,18,19,20-tetranor-;
2a,2b-Dihomo-16-(p-fluorophenoxy)-17,18,19,20-tetranor-;
2a,2b-Dihomo-16-phenoxy-18,19,20-trinor-;
2a,2b-Dihomo-16-methyl-16-phenoxy-18,19,20-trinor-;
2a,2b-Dihomo-15-methyl-13,14-didehydro-;
2a,2b-Dihomo-16-methyl-13,14-didehydro-;
2a,2b-Dihomo-16,16-dimethyl-13,14-didehydro-;
2a,2b-Dihomo-16-fluoro-13,14-didehydro-;
2a,2b-Dihomo-16,16-difluoro-13,14-didehydro-;
2a,2b-Dihomo-17-phenyl-18,19,20-trinor-13,14-didehydro-;

2a,2b-Dihomo-17-(m-trifluoromethylphenyl)-18,19,20-trinor-13,14-didehydro-;
2a,2b-Dihomo-17-(m-chlorophenyl)-18,19,20-trinor-13,14-didehydro-;
2a,2b-Dihomo-17-(p-fluorophenyl)-18,19,20-trinor-13,14-didehydro-;
2a,2b-Dihomo-16-methyl-17-phenyl-18,19,20-trinor-13,14-didehydro-;
2a,2b-Dihomo-16,16-dimethyl-17-phenyl-18,19,20-trinor-13,14-didehydro-;
2a,2b-Dihomo-16-fluoro-17-phenyl-18,19,20-trinor-13,14-didehydro-;
2a,2b-Dihomo-16,16-difluoro-17-phenyl-18,19,20-trinor-13,14-didehydro-;
2a,2b-Dihomo-16-phenyl-17,18,19,20-tetranor-13,14-didehydro-;
2a,2b-Dihomo-16-(m-trifluoromethylphenyl)-17,18,19,20-tetranor-13,14-didehydro-;
2a,2b-Dihomo-16-(m-chlorophenyl)-17,18,19,20-tetranor-13,14-didehydro-;
2a,2b-Dihomo-16-(p-fluorophenyl)-17,18,19,20-tetranor-13,14-didehydro-;
2a,2b-Dihomo-16-phenyl-18,19,20-trinor-13,14-didehydro-;
2a,2b-Dihomo-16-methyl-16-phenyl-18,19,20-trinor-13,14-didehydro-;
2a,2b-Dihomo-16-phenoxy-17,18,19,20-tetranor-13,14-didehydro-;
2a,2b-Dihomo-16-(m-trifluoromethylphenoxy)-17,18,19,20-tetranor-13,14-didehydro-;
2a,2b-Dihomo-16-(m-chlorophenoxy)-17,18,19,20-tetranor-13,14-didehydro-;
2a,2b-Dihomo-16-(p-fluorophenoxy)-17,18,19,20-tetranor-13,14-didehydro-;
2a,2b-Dihomo-16-phenoxy-18,19,20-trinor-13,14-didehydro-;
2a,2b-Dihomo-16-methyl-16-phenoxy-18,19,20-trinor-13,14-didehydro-;
2a,2b-Dihomo-13,14-dihydro-;
2a,2b-Dihomo-15-methyl-13,14-dihydro-;
2a,2b-Dihomo-16-methyl-13,14-dihydro-;
2a,2b-Dihomo-16,16-dimethyl-13,14-dihydro-;
2a,2b-Dihomo-16-fluoro-13,14-dihydro-;
2a,2b-Dihomo-16,16-difluoro-13,14-dihydro-;
2a,2b-Dihomo-17-phenyl-18,19,20-trinor-13,14-dihydro-;
2a,2b-Dihomo-17-(m-trifluoromethylphenyl)-18,19,20-trinor-13,14-dihydro-;
2a,2b-Dihomo-17-(m-chlorophenyl)-18,19,20-trinor-13,14-dihydro-;
2a,2b-Dihomo-17-(p-fluorophenyl)-18,19,20-trinor-13,14-dihydro-;
2a,2b-Dihomo-16-methyl-17-phenyl-18,19,20-trinor-13,14-dihydro-;
2a,2b-Dihomo-16,16-dimethyl-17-phenyl-18,19,20-trinor-13,14-dihydro-;
2a,2b-Dihomo-16-fluoro-17-phenyl-18,19,20-trinor-13,14-dihydro-;
2a,2b-Dihomo-16,16-difluoro-17-phenyl-18,19,20-trinor-13,14-dihydro-;
2a,2b-Dihomo-16-phenyl-17,18,19,20-tetranor-13,14-dihydro-;
2a,2b-Dihomo-16-(m-trifluoromethylphenyl)-17,18,19,20-tetranor-13,14-dihydro-;
2a,2b-Dihomo-16-(m-chlorophenyl)-17,18,19,20-tetranor-13,14-dihydro-;
2a,2b-Dihomo-16-(p-fluorophenyl)-17,18,19,20-tetranor-13,14-dihydro-;
2a,2b-Dihomo-16-phenyl-18,19,20-trinor-13,14-dihydro-;
2a,2b-Dihomo-16-methyl-16-phenyl-18,19,20-trinor-13,14-dihydro-;
2a,2b-Dihomo-16-phenoxy-17,18,19,20-tetranor-13,14-dihydro-;
2a,2b-Dihomo-16-(m-trifluoromethylphenoxy)-17,18,19,20-tetranor-13,14-dihydro-;
2a,2b-Dihomo-16-(m-chlorophenoxy)-17,18,19,20-tetranor-13,14-dihydro-;
2a,2b-Dihomo-16-(p-fluorophenoxy)-17,18,19,20-tetranor-13,14-dihydro-;
2a,2b-Dihomo-16-methyl-16-phenoxy-18,19,20-trinor-13,14-dihydro-;
2a,2b-Dihomo-15-epi-13-cis-;
2a,2b-Dihomo-15-methyl-15-epi-13-cis-;
2a,2b-Dihomo-16-methyl-15-epi-13-cis-;
2a,2b-Dihomo-16,16-dimethyl-15-epi-13-cis-;
2a,2b-Dihomo-16-fluoro-15-epi-13-cis-;
2a,2b-Dihomo-16,16-difluoro-15-epi-13-cis-;
2a,2b-Dihomo-17-phenyl-18,19,20-trinor-15-epi-13-cis-;
2a,2b-Dihomo-17-(m-trifluoromethylphenyl)-18,19,20-trinor-13-cis-;
2a,2b-Dihomo-17-(m-chlorophenyl)-18,19,20-trinor-15-epi-13-cis-;
2a,2b-Dihomo-17-(p-fluorophenyl-18,19,20-trinor-15-epi-13-cis-;
2a,2b-Dihomo-16-methyl-17-phenyl-18,19,20-trinor-15-epi-13-cis-;
2a,2b-Dihomo-16,16-dimethyl-17-phenyl-18,19,20-trinor-15-epi-13-cis-;
2a,2b-Dihomo-16-fluoro-17-phenyl-18,19,20-trinor-15-epi-13-cis-;
2a,2b-Dihomo-16,16-difluoro-17-phenyl-18,19,20-trinor-15-epi-13-cis-;
2a,2b-Dihomo-16-phenyl-17,18,19,20-tetranor-15-epi-13-cis-;
2a,2b-Dihomo-16-(m-trifluoromethylphenyl)-17,18,19,20-tetranor-15-epi-13-cis-;
2a,2b-Dihomo-16-(m-chlorophenyl)-17,18,19,20-tetranor-15-epi-13-cis-;
2a,2b-Dihomo-16-(p-fluorophenyl)-17,18,19,20-tetranor-15-epi-13-cis-;
2a,2b-Dihomo-16-phenyl-18,19,20-trinor-15-epi-13-cis-;
2a,2b-Dihomo-16-methyl-16-phenyl-18,19,20-trinor-15-epi-13-cis-;
2a,2b-Dihomo-16-phenoxy-17,18,19,20-tetranor-15-epi-13-cis-;
2a,2b-Dihomo-16-(m-trifluoromethylphenoxy)-17,18,19,20-tetranor-15-epi-13-cis-;
2a,2b-Dihomo-16-(m-chlorophenoxy)-17,18,19,20-tetranor-15-epi-13-cis-;
2a,2b-Dihomo-16-(p-fluorophenoxy-17,18,19,20-tetranor-15-epi-13-cis-;
2a,2b-Dihomo-16-phenoxy-18,19,20-trinor-15-epi-13-cis-;
2a,2b-Dihomo-16-methyl-16-phenoxy-18,19,20-trinor-15-epi-13-cis-;
5,6-Didehydro-;
5,6-Didehydro-16-methyl-;
5,6-Didehydro-16,16-dimethyl-;
5,6-Didehydro-16-fluoro-;
5,6-Didehydro-16,16-difluoro-;
5,6-Didehydro-17-phenyl-18,19,20-trinor-;
5,6-Didehydro-17-(m-trifluoromethylphenyl)-18,19,20-trinor-;
5,6-Didehydro-17-(m-chlorophenyl)-18,19,20-trinor-;
5,6-Didehydro-17-(p-fluorophenyl)-18,19,20-trinor-;

5,6-Didehydro-16-methyl-17-phenyl-18,19,20-trinor-;
5,6-Didehydro-16,16-dimethyl-17-phenyl-18,19,20-trinor-;
5,6-Didehydro-16-fluoro-17-phenyl-18,19,20-trinor-;
5,6-Didehydro-16,16-difluoro-17-phenyl-18,19,20-trinor-;
5,6-Didehydro-16-phenyl-17,18,19,20-tetranor-;
5,6-Didehydro-16-(m-trifluoromethylphenyl)-17,18,19,20-tetranor-;
5,6-Didehydro-16-(m-chlorophenyl)-17,18,19,20-tetranor-;
5,6-Didehydro-16-(p-fluorophenyl)-17,18,19,20-tetranor-;
5,6-Didehydro-16-phenyl-18,19,20-trinor-;
5,6-Didehydro-16-methyl-16-phenyl-18,19,20-trinor-;
5,6-Didehydro-16-phenoxy-17,18,19,20-tetranor-;
5,6-Didehydro-16-(m-trifluoromethylphenoxy)-17,18,19,20-tetranor-;
5,6-Didehydro-16-(m-chlorophenoxy)-17,18,19,20-tetranor-;
5,6-Didehydro-16-(p-fluorophenoxy)-17,18,19,20-tetranor-;
5,6-Didehydro-16-phenoxy-18,19,20-trinor-;
5,6-Didehydro-16-methyl-16-phenoxy-18,19,20-trinor-;
5,6-Didehydro-15-methyl-13,14-didehydro-;
5,6-Didehydro-16-methyl-13,14-didehydro-;
5,6-Didehydro-16,16-dimethyl-13,14-didehydro-;
5,6-Didehydro-16-fluoro-13,14-didehydro-;
5,6-Didehydro-16,16-difluoro-13,14-didehydro-;
5,6-Didehydro-17-phenyl-18,19,20-trinor-13,14-didehydro-;
5,6-Didehydro-17-(m-trifluoromethylphenyl)-18,19,20-trinor-13,14-didehydro-;
5,6-Didehydro-17-(m-chlorophenyl)-18,19,20-trinor-13,14-didehydro-;
5,6-Didehydro-17-(p-fluorophenyl)-18,19,20-trinor-13,14-didehydro-;
5,6-Didehydro-16-methyl-17-phenyl-18,19,20-trinor-13,14-didehydro-;
5,6-Didehydro-16,16-dimethyl-17-phenyl-18,19,20-trinor-13,14-didehydro-;
5,6-Didehydro-16-fluoro-17-phenyl-18,19,20-trinor-13,14-didehydro-;
5,6-Didehydro-16,16-difluoro-17-phenyl-18,19,20-trinor-13,14-didehydro-;
5,6-Didehydro-16-phenyl-17,18,19,20-tetranor-13,14-didehydro-;
5,6-Didehydro-16-(m-trifluoromethylphenyl)-17,18,19,20-tetranor-13,14-didehydro-;
5,6-Didehydro-16-(m-chlorophenyl)-17,18,19,20-tetranor-13,14-didehydro-;
5,6-Didehydro-16-(p-fluorophenyl)-17,18,19,20-tetranor-13,14-didehydro-;
5,6-Didehydro-16-phenyl-18,19,20-trinor-13,14-didehydro-;
5,6-Didehydro-16-methyl-16-phenyl-18,19,20-trinor-13,14-didehydro-;
5,6-Didehydro-16-phenoxy-17,18,19,20-tetranor-13,14-didehydro-;
5,6-Didehydro-16-(m-trifluoromethylphenoxy)-17,18,19,20-tetranor-13,14-didehydro-;
5,6-Didehydro-16-(m-chlorophenoxy)-17,18,19,20-tetranor-13,14-didehydro-;
5,6-Didehydro-16-(p-fluorophenoxy)-17,18,19,20-tetranor-13,14-didehydro-;
5,6-Didehydro-16-phenoxy-18,19,20-trinor-13,14-didehydro-;
5,6-Didehydro-16-methyl-16-phenoxy-18,19,20-trinor-13,14-didehydro-;
5,6-Didehydro-13,14-dihydro-;
5,6-Didehydro-15-methyl-13,14-dihydro-;
5,6-Didehydro-16-methyl-13,14-dihydro-;
5,6-Didehydro-16,16-dimethyl-13,14-dihydro-;
5,6-Didehydro-16-fluoro-13,14-dihydro-;
5,6-Didehydro-16,16-difluoro-13,14-dihydro-;
5,6-Didehydro-17-phenyl-18,19,20-trinor-13,14-dihydro-;
5,6-Didehydro-17-(m-trifluoromethylphenyl)-18,19,20-trinor-13,14-dihydro-;
5,6-Didehydro-17-(m-chlorophenyl)-18,19,20-trinor-13,14-dihydro-;
5,6-Didehydro-17-(p-fluorophenyl)-18,19,20-trinor-13,14-dihydro-;
5,6-Didehydro-16-methyl-17-phenyl-18,19,20-trinor-13,14-dihydro-;
5,6-Didehydro-16,16-dimethyl-17-phenyl-18,19,20-trinor-13,14-dihydro-;
5,6-Didehydro-16-fluoro-17-phenyl-18,19,20-trinor-13,14-dihydro-;
5,6-Didehydro-16,16-difluoro-17-phenyl-18,19,20-trinor-13,14-dihydro-;
5,6-Didehydro-16-phenyl-17,18,19,20-tetranor-13,14-dihydro-;
5,6-Didehydro-16-(m-trifluoromethylphenyl)-17,18,19,20-tetranor-13,14-dihydro-;
5,6-Didehydro-16-(m-chlorophenyl)-17,18,19,20-tetranor-13,14-dihydro-;
5,6-Didehydro-16-(p-fluorophenyl)-17,18,19,20-tetranor-13,14-dihydro-;
5,6-Didehydro-16-phenyl-18,19,20-trinor-13,14-dihydro-;
5,6-Didehydro-16-methyl-16-phenyl-18,19,20-trinor-13,14-dihydro-;
5,6-Didehydro-16-phenoxy-17,18,19,20-tetranor-13,14-dihydro-;
5,6-Didehydro-16-(m-trifluoromethylphenoxy)-17,18,19,20-tetranor-13,14-dihydro-;
5,6-Didehydro-16-(m-chlorophenoxy)-17,18,19,20-tetranor-13,14-dihydro-;
5,6-Didehydro-16-(p-fluorophenoxy)-17,18,19,20-tetranor-13,14-dihydro-;
5,6-Didehydro-16-methyl-16-phenoxy-18,19,20-trinor-13,14-dihydro-;
5,6-Didehydro-15-epi-13-cis-;
5,6-Didehydro-15-methyl-15-epi-13-cis-;
5,6-Didehydro-16-methyl-15-epi-13-cis-;
5,6-Didehydro-16,16-dimethyl-15-epi-13-cis-;
5,6-Didehydro-16-fluoro-15-epi-13-cis-;
5,6-Didehydro-16,16-difluoro-15-epi-13-cis-;
5,6-Didehydro-17-phenyl-18,19,20-trinor-15-epi-13-cis-;
5,6-Didehydro-17-(m-trifluoromethylphenyl)-18,19,20-trinor-15-epi-13-cis-;
5,6-Didehydro-17-(m-chlorophenyl)-18,19,20-trinor-15-epi-13-cis-;
5,6-Didehydro-17-(p-fluorophenyl)-18,19,20-trinor-15-epi-13-cis-;
5,6-Didehydro-16-methyl-17-phenyl-18,19,20-trinor-15-epi-13-cis-;
5,6-Didehydro-16,16-dimethyl-17-phenyl-18,19,20-trinor-15-epi-13-cis-;
5,6-Didehydro-16-fluoro-17-phenyl-18,19,20-trinor-15-epi-13-cis-;
5,6-Didehydro-16,16-difluoro-17-phenyl-18,19,20-trinor-15-epi-13-cis-;

5,6-Didehydro-16-phenyl-17,18,19,20-tetranor-15-epi-13-cis-;
5,6-Didehydro-16-(m-trifluoromethylphenyl)-17,18,19,20-tetranor-15-epi-13-cis-;
5,6-Didehydro-16-(m-chlorophenyl)-17,18,19,20-tetranor-15-epi-13-cis-;
5,6-Didehydro-16-(p-fluorophenyl)-17,18,19,20-tetranor-15-epi-13-cis-;
5,6-Didehydro-16-phenyl-18,19,20-trinor-15-epi-13-cis-;
5,6-Didehydro-16-methyl-16-phenyl-18,19,20-trinor-15-epi-13-cis-;
5,6-Didehydro-16-phenoxy-17,18,19,20-tetranor-15-epi-13-cis-;
5,6-Didehydro-16-(m-trifluoromethylphenoxy)-17,18,19,20-tetranor-15-epi-13-cis-;
5,6-Didehydro-16-(m-chlorophenoxy)-17,18,19,20-tetranor-15-epi-13-cis-;
5,6-Didehydro-16-(p-fluorophenoxy)-17,18,19,20-tetranor-15-epi-13-cis-;
5,6-Didehydro-16-phenoxy-18,19,20-trinor-15-epi-13-cis-;
5,6-Didehydro-16-methyl-16-phenoxy-18,19,20-trinor-15-epi-13-cis-;
2,2-Difluoro-;
2,2-Difluoro-16-methyl-;
2,2-Difluoro-16,16-dimethyl-;
2,2,16-Trifluoro-;
2,2,16,16-Tetrafluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2,16-Trifluoro-17-phenyl-18,19,20-trinor-;
2,2,16,16-Tetrafluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,18,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-15-methyl-13,14-didehydro-;
2,2-Difluoro-16-methyl-13,14-didehydro-;
2,2-Difluoro-16,16-dimethyl-13,14-didehydro-;
2,2,16-Trifluoro-13,14-didehydro-;
2,2,16,16-Tetrafluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-(p-fluorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-(p-fluorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-15-methyl-13,14-dihydro-;
2,2-Difluoro-16-methyl-13,14-dihydro-;
2,2-16,16-dimethyl-13,14-dihydro-;
b 2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;

2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-methyl-16-phenoxy-18,19,20-trinor-13,14-dihydro-;
2,2-Difluoro-15-epi-13-cis-;
2,2-Difluoro-15-methyl-15-epi-13-cis-;
2,2-Difluoro-16,16-dimethyl-15-epi-13-cis-;
2,2,16-Trifluoro-15-epi-13-cis-;
2,2,16,16-Tetrafluoro-15-epi-13-cis-;
2,2-Difluoro-17-phenyl-18,19,20-trinor-15-epi-13-cis-;
2,2-Difluoro-17-(m-trifluoromethylphenyl)-18,19,20-trinor-15-epi-13-cis-;
2,2-Difluoro-17-(m-chlorophenyl)-18,19,20-trinor-15-epi-13-cis-;
2,2-Difluoro-17-(p-fluorophenyl)-18,19,20-trinor-15-epi-13-cis-;
2,2-Difluoro-16-methyl-17-phenyl-18,19,20-trinor-15-epi-13-cis-;
2,2-Difluoro-16,16-dimethyl-17-phenyl-18,19,20-trinor-15-epi-13-cis-;
2,2,16-Trifluoro-17-phenyl-18,19,20-trinor-15-epi-13-cis-;
2,2,16,16-Tetrafluoro-17-phenyl-18,19,20-trinor-15-epi-13-cis-;
2,2-Difluoro-16-phenyl-17,18,19,20-tetranor-15-epi-13-cis-;
2,2-Difluoro-16-(m-trifluoromethylphenyl)-17,18,19,20-tetranor-15-epi-13-cis-;
2,2-Difluoro-16-(m-chlorophenyl)-17,18,19,20-tetranor-15-epi-13-cis-;
2,2-Difluoro-16-(p-fluorophenyl)-17,18,19,20-tetranor-15-epi-13-cis-;
2,2-Difluoro-16-phenyl-18,19,20-trinor-15-epi-13-cis-;
2,2-Difluoro-16-methyl-16-phenyl-18,19,20-trinor-15-epi-13-cis-;
2,2-Difluoro-16-phenoxy-17,18,19,20-tetranor-15-epi-13-cis-;
2,2-Difluoro-16-(m-trifluoromethylphenoxy)-17,18,19,20-tetranor-15-epi-13-cis-;
2,2-Difluoro-16-(m-chlorophenoxy)-17,18,19,20-tetranor-15-epi-13-cis-;
2,2-Difluoro-16-(p-fluorophenoxy)-17,18,19,20-tetranor-15-epi-13-cis-;
2,2-Difluoro-16-phenoxy-18,19,20-trinor-15-epi-13-cis-;
2,2-Difluoro-16-methyl-16-phenoxy-1-,19,20-trinor-15-epi-13-cis-.

Following the procedure of Examples 1–4, but employing the appropriate PGE$_1$-type or 8β,12α-PGE$_1$-type starting material, there are prepared
2-Decarboxy-2-methylcarbonyl-9-deoxy-9-methylene-PGF$_1$-type compounds; or
2-Decarboxy-2-methylcarbonyl-9-deoxy-9-methylene-8β,12α-PGF$_1$-type compounds; which exhibit the following side chain characteristics:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-13,14-didehydro-;
16,16-Dimethyl-16-phenoxy-18,19,20-trinor-;
13,14-Didehydro-;
15-Methyl-13,14-didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-(p-fluorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenyl)-17,18,19,20-tetranor-13,14-didehydro-;
16-(p-fluorophenyl)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
15-Methyl-13,14-dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;

17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
15-epi-13-cis-;
16-Methyl-15-epi-13-cis-;
16,16-Dimethyl-15-epi-13-cis-;
16-Fluoro-15-epi-13-cis-;
16,16-Difluoro-15-epi-13-cis-;
17-Phenyl-18,19,20-trinor-15-epi-13-cis-;
17-(m-trifluoromethylphenyl)-18,19,20-trinor-15-epi-13-cis-;
17-(m-chlorophenyl)-18,19,20-trinor-15-epi-13-cis-;
17-(p-fluorophenyl)-18,19,20-trinor-15-epi-13-cis-;
16-Methyl-17-phenyl-18,19,20-trinor-15-epi-13-cis-;
16,16-Dimethyl-17-phenyl-18,19,20-trinor-15-epi-13-cis-;
16-Fluoro-17-phenyl-18,19,20-trinor-15-epi-13-cis-;
16,16-Difluoro-17-phenyl-18,19,20-trinor-15-epi-13-cis-;
16-Phenyl-17,18,19,20-tetranor-15-epi-13-cis-;
;b  16-(m-trifluoromethylphenyl)-17,18,19,20-tetranor-15-epi-13-cis-;
16-(m-chlorophenyl)-17,18,19,20-tetranor-15-epi-13-cis-;
16-(p-fluorophenyl)-17,18,19,20-tetranor-15-epi-13-cis-;
16-Phenyl-18,19,20-trinor-15-epi-13-cis-;
16-Methyl-16-phenyl-18,19,20-trinor-15-epi-13-cis-;
16-Phenoxy-17,18,19,20-tetranor-15-epi-13-cis-;
16-(m-trifluoromethylphenoxy)-17,18,19,20-tetranor-15-epi-13-cis-;
16-(m-chlorophenoxy)-17,18,19,20-tetranor-15-epi-13-cis-;
16-(p-fluorophenoxy)-17,18,19,20-tetranor-15-epi-13-cis-;
16-Phenoxy-18,19,20-trinor-15-epi-13-cis-;
16-Methyl-16-phenoxy-18,19,20-trinor-15-epi-13-cis-;
2a,2b-Dihomo-;
2a,2b-Dihomo-15-methyl-;
2a,2b-Dihomo-16-methyl-;
2a,2b-Dihomo-16,16-dimethyl-;
2a,2b-Dihomo-16-fluoro-;
2a,2b-Dihomo-16,16-difluoro-;
2a,2b-Dihomo-17-phenyl-18,19,20-trinor-;
2a,2b-Dihomo-17-(m-trifluoromethylphenyl)-18,19,20-trinor-;
2a,2b-Dihomo-17-(m-chlorophenyl)-18,19,20-trinor-;
2a,2b-Dihomo-17-(p-fluorophenyl)-18,19,20-trinor-;
2a,2b-Dihomo-16-methyl-17-phenyl-18,19,20-trinor-;
2a,2b-Dihomo-16,16-dimethyl-17-phenyl-18,19,20-trinor-;
2a,2b-Dihomo-16-fluoro-17-phenyl-18,19,20-trinor-;
2a,2b-Dihomo-16,16-difluoro-17-phenyl-18,19,20-trinor-;
2a,2b-Dihomo-16-phenyl-17,18,19,20-tetranor-;
2a,2b-Dihomo-16-(m-trifluoromethylphenyl)-17,18,19,20-tetranor-;
2a,2b-Dihomo-16-(m-chlorophenyl)-17,18,19,20-tetranor-;
2a,3b-Dihomo-16-(p-fluorophenyl)-17,18,19,20-tetranor-;
2a,2b-Dihomo-16-phenyl-18,19,20-trinor-;
2a,2b-Dihomo-16-methyl-16-phenyl-18,19,20-trinor-;
2a,2b-Dihomo-16-phenoxy-17,18,19,20-tetranor-;
2a,2b-Dihomo-16-(m-trifluoromethylphenoxy)-17,18,19,20-tetranor-;
2a,2b-Dihomo-16-(m-chlorophenoxy)-17,18,19,20-tetranor-;
2a,2b-Dihomo-16-(p-fluorophenoxy)-17,18,19,20-tetranor-;
2a,2b-Dihomo-16-phenoxy-18,19,20-trinor-;
2a,2b-Dihomo-16-methyl-16-phenoxy-18,19,20-trinor-;
2a,2b-Dihomo-15-methyl-13,14-didehydro-;
2a,2b-Dihomo-16-methyl-13,14-didehydro-;
2a,2b-Dihomo-16,16-dimethyl-13,14-didehydro-;
2a,2b-Dihomo-16-fluoro-13,14-didehydro-;
2a,2b-Dihomo-16,16-difluoro-13,14-didehydro-;
2a,2b-Dihomo-17-phenyl-18,19,20-trinor-13,14-didehydro-;
2a,2b-Dihomo-17-(m-trifluoromethylphenyl)-18,19,20-trinor-13,14-didehydro-;
2a,2b-Dihomo-17-(m-chlorophenyl)-18,19,20-trinor-13,14-didehydro-;
2a,2b-Dihomo-17-(p-fluorophenyl)-18,19,20-trinor-13,14-didehydro-;
2a,2b-Dihomo-16-methyl-17-phenyl-18,19,20-trinor-13,14-didehydro-;
2a,2b-Dihomo-16,16-dimethyl-17-phenyl-18,19,20-trinor-13,14-didehydro-;
2a,2b-Dihomo-16-fluoro-17-phenyl-18,19,20-trinor-13,14-didehydro-;
2a,2b-Dihomo-16,16-difluoro-17-phenyl-18,19,20-trinor-13,14-didehydro-;
2a,2b-Dihomo-16-phenyl-17,18,19,20-tetranor-13,14-didehydro-;
2a,2b-Dihomo-16-(m-trifluoromethylphenyl)-17,18,19,20-tetranor-13,14-didehydro-;
2a,2b-Dihomo-16-(m-chlorophenyl)-17,18,19,20-tetranor-13,14-didehydro-;
2a,2b-Dihomo-16-(p-fluorophenyl)-17,18,19,20-tetranor-13,14-didehydro-;
2a,2b-Dihomo-16-phenyl-18,19,20-trinor-13,14-didehydro-;
2a,2b-Dihomo-16-methyl-16-phenyl-18,19,20-trinor-13,14-didehydro-;
2a,2b-Dihomo-16-phenoxy-17,18,19,20-tetranor-13,14-didehydro-;
2a,2b-Dihomo-16-(m-trifluoromethylphenoxy)-17,18,19,20-tetranor-13,14-didehydro-;
2a,2b-Dihomo-16-(m-chlorophenoxy)-17,18,19,20-tetranor-13,14-didehydro-;

2a,2b-Dihomo-16-(p-fluorophenoxy)-17,18,19,20-tetranor-13,14-didehydro-;
2a,2b-Dihomo-16-phenoxy-18,19,20-trinor-13,14-didehydro-;
2a,2b-Dihomo-16-methyl-16-phenoxy-18,19,20-trinor-13,14-didehydro-;
2a,2b-Dihomo-13,14-dihydro-;
2a,2b-Dihomo-15-methyl-13,14-dihydro-;
2a,2b-Dihomo-16-methyl-13,14-dihydro-;
2a,2b-Dihomo-16,16-dimethyl-13,14-dihydro-;
2a,2b-Dihomo-16-fluoro-13,14-dihydro-;
2a,2b-Dihomo-16,16-Difluoro-13,14-dihydro-;
2a,2b-Dihomo-17-phenyl-18,19,20-trinor-13,14-dihydro-;
2a,2b-Dihomo-17-(m-trifluoromethylphenyl)-18,19,20-trinor-13,14-dihydro-;
2a,2b-Dihomo-17-(m-chlorophenyl)-18,19,20-trinor-13,14-dihydro-;
2a,2b-Dihomo-17-(p-fluorophenyl)-18,19,20-trinor-13,14-dihydro-;
2a,2b-Dihomo-16-methyl-17-phenyl-18,19,20-trinor-13,14-dihydro-;
2a,2b-Dihomo-16,16-dimethyl-17-phenyl-18,19,20-trinor-13,14-dihydro-;
2a,2b-Dihomo-16-fluoro-17-phenyl-18,19,20-trinor-13,14-dihydro-;
2a,2b-Dihomo-16,16-difluoro-17-phenyl-18,19,20-trinor-13,14-dihydro-;
2a,2b-Dihomo-16-phenyl-17,18,19,20-tetranor-13,14-dihydro-;
2a,2b-Dihomo-16-(m-trifluoromethylphenyl)-17,18,19,20-tetranor-13,14-dihydro-;
2a,2b-Dihomo-16-(m-chlorophenyl)-17,18,19,20-tetranor-13,14-dihydro-;
2a,2b-Dihomo-16-(p-fluorophenyl)-17,18,19,20-tetranor-13,14-dihydro-;
2a,2b-Dihomo-16-phenyl-18,19,20-trinor-13,14-dihydro-;
2a,2b-Dihomo-16-methyl-16-phenyl-18,19,20-trinor-13,14-dihydro-;
2a,2b-Dihomo-16-phenoxy-17,18,19,20-tetranor-13,14-dihydro-;
2a,2b-Dihomo-16-(m-trifluoromethylphenoxy)-17,18,19,20-tetranor-13,14-dihydro-;
2a,2b-Dihomo-16-(m-chlorophenoxy)-17,18,19,20-tetranor-13,14-dihydro-;
2a,2b-Dihomo-16-(p-fluorophenoxy)-17,18,19,20-tetranor-13,14-dihydro-;
2a,2b-Dihomo-16-methyl-16-phenoxy-18,19,20-trinor-13,14-dihydro-;
2a,2b-Dihomo-15-epi-13-cis-;
2a,2b-Dihomo-15-methyl-15-epi-13-cis-;
2a,2b-Dihomo-16-methyl-15-epi-13-cis-;
2a,2b-Dihomo-16,16-dimethyl-15-epi-13-cis-;
2a,2b-Dihomo-16-fluoro-15-epi-13-cis-;
2a,2b-Dihomo-16,16-difluoro-15-epi-13-cis-;
2a,2b-Dihomo-17-phenyl-18,19,20-trinor-15-epi-13-cis-;
2a,2b-Dihomo-17-(m-trifluoromethylphenyl)-18,19,20-trinor-15-epi-13-cis-;
2a,2b-Dihomo-17-(m-chlorophenyl)-18,19,20-trinor-15-epi-13-cis-;
2a,2b-Dihomo-17-(p-fluorophenyl)-18,19,20-trinor-15-epi-13-cis-;
2a,2b-Dihomo-16-methyl-17-phenyl-18,19,20-trinor-15-epi-13-cis-;
2a,2b-Dihomo-16,16-dimethyl-17-phenyl-18,19,20-trinor-15-epi-13-cis-;
2a,2b-Dihomo-16-fluoro-17-phenyl-18,19,20-trinor-15-epi-13-cis-;
2a,2b-Dihomo-16,16-difluoro-17-phenyl-18,19,20-trinor-15-epi-13-cis-;
2a,2b-Dihomo-16-phenyl-17,18,19,20-tetranor-15-epi-13-cis-;
2a,2b-Dihomo-16-(m-trifluoromethylphenyl)-17,18,19,20-tetranor-15-epi-13-cis-;
2a,2b-Dihomo-16-(m-chlorophenyl)-17,18,19,20-tetranor-15-epi-13-cis-;
2a,2b-Dihomo-(p-fluorophenyl)-17,18,19,20-tetranor-15-epi-13-cis-;
2a,2b-Dihomo-16-phenyl-18,19,20-trinor-15-epi-13-cis-;
2a,2b-Dihomo-16-methyl-16-phenyl-18,19,20-trinor-15-epi-13-cis-;
2a,2b-Dihomo-16-phenoxy-17,18,19,20-tetranor-15-epi-13-cis-;
2a,2b-Dihomo-16-(m-trifluoromethylphenoxy)-17,18,19,20-tetranor-15-epi-13-cis-;
2a,2b-Dihomo-16-(m-chlorophenoxy)-17,18,19,20-tetranor-15-epi-13-cis-;
2a,2b-Dihomo-16-(p-fluorophenoxy)-17,18,19,20-tetranor-15-epi-13-cis-;
2a,2b-Dihomo-16-phenoxy-18,19,20-trinor-15-epi-13-cis-;
2a,2b-Dihomo-16-methyl-16-phenoxy-18,19,20-trinor-15-epi-13-cis-;
cis-4,5-Didehydro-;
cis-4,5-Didehydro-15-methyl-;
cis-4,5-Didehydro-16-methyl-;
cis-4,5-Didehydro-16,16-dimethyl-;
cis-4,5-Didehydro-16-fluoro-;
cis-4,5-Didehydro-16,16-difluoro-;
cis-4,5-Didehydro-17-phenyl-18,19,20-trinor-;
cis-4,5-Didehydro-17-(m-trifluoromethylphenyl)-18,19,20-trinor-;
cis-4,5-Didehydro-17-(m-chlorophenyl)-18,19,20-trinor-;
cis-4,5-Didehydro-17-(p-fluorophenyl)-18,19,20-trinor-;
cis-4,5-Didehydro-16-methyl-17-phenyl-18,19,20-trinor-;
cis-4,5-Didehydro-16,16-dimethyl-17-phenyl-18,19,20-trinor-;
cis-4,5-Didehydro-16-fluoro-17-phenyl-18,19,20-trinor-;
cis-4,5-Didehydro-16,16-difluoro-17-phenyl-18,19,20-trinor-;
cis-4,5-Didehydro-16-phenyl-17,18,19,20-tetranor-;
cis-4,5-Didehydro-16-(m-trifluoromethylphenyl)-17,18,19,20-tetranor-;
cis-4,5-Didehydro-16-(m-chlorophenyl)-17,18,19,20-tetranor-;
cis-4,5-Didehydro-16-(p-fluorophenyl)-17,18,19,20-tetranor-;
cis-4,5-Didehydro-16-phenyl-18,19,20-trinor-;
cis-4,5-Didehydro-16-methyl-16-phenyl-18,19,20-trinor-;
cis-4,5-Didehydro-16-phenoxy-17,18,19,20-tetranor-;
cis-4,5-Didehydro-16-(m-trifluoromethylphenoxy)-17,18,19,20-tetranor-;
cis-4,5-Didehydro-16-(m-chlorophenoxy)-17,18,19,20-tetranor-;
cis-4,5-Didehydro-16-(p-fluorophenoxy)-17,18,19,20-tetranor-;
cis-4,5-Didehydro-16-phenoxy-18,19,20-trinor-;
cis-4,5-Didehydro-16-methyl-16-phenoxy-18,19,20-trinor-;
cis-4,5-Didehydro-15-methyl-13,14-didehydro-;
cis-4,5-Didehydro-16-methyl-13,14-didehydro-;

cis-4,5-Didehydro-16,16-dimethyl-13,14-didehydro-;
cis-4,5-Didehydro-16-fluoro-13,14-didehydro-;
cis-4,5-Didehydro-16,16-difluoro-13,14-didehydro-;
cis-4,5-Didehydro-17-phenyl-18,19,20-trinor-13,14-didehydro-;
cis-4,5-Didehydro-17-(m-trifluoromethylphenyl)-18,19,20-trinor-13,14-didehydro-;
cis-4,5-Didehydro-17-(m-chlorophenyl)-18,19,20-trinor-13,14-didehydro-;
cis-4,5-Didehydro-17-(p-fluorophenyl)-18,19,20-trinor-13,14-didehydro-;
cis-4,5-Didehydro-16-methyl-17-phenyl-18,19,20-trinor-13,14-didehydro-;
cis-4,5-Didehydro-16,16-dimethyl-17-phenyl-18,19,20-trinor-13,14-didehydro-;
cis-4,5-Didehydro-16-fluoro-17-phenyl-18,19,20-trinor-13,14-didehydro-;
cis-4,5-Didehydro-16,16-difluoro-17-phenyl-18,19,20-trinor-13,14-didehydro-;
cis-4,5-Didehydro-16-phenyl-17,18,19,20-tetranor-13,14-didehydro-;
cis-4,5-Didehydro-16-(m-trifluoromethylphenyl)-17,18,19,20-tetranor-13,14-didehydro-;
cis-4,5-Didehydro-16-(m-chlorophenyl)-17,18,19,20-tetranor-13,14-didehydro-;
cis-4,5-Didehydro-16-(p-fluorophenyl)-17,18,19,20-tetranor-13,14-didehydro-;
cis-4,5-Didehydro-16-phenyl-18,19,20-trinor-13,14-didehydro-;
cis-4,5-Didehydro-16-methyl-16-phenyl-18,19,20-trinor-13,14-didehydro-;
cis-4,5-Didehydro-16-phenoxy-17,18,19,20-tetranor-13,14-didehydro-;
cis-4,5-Didehydro-16-(m-trifluoromethylphenoxy)-17,18,19,20-tetranor-13,14-didehydro-;
cis-4,5-Didehydro-16-(m-chlorophenoxy)-17,18,19,20-tetranor-13,14-didehydro-;
cis-4,5-Didehydro-16-(p-fluorophenoxy)-17,18,19,20-tetranor-13,14-didehydro-;
cis-4,5-Didehydro-16-phenoxy-18,19,20-trinor-13,14-didehydro-;
cis-4,5-Didehydro-16-methyl-16-phenoxy-18,19,20-trinor-13,14-didehydro-;
cis-4,5-Didehydro-13,14-dihydro-;
cis-4,5-Didehydro-15-methyl-13,14-dihydro-;
cis-4,5-Didehydro-16-methyl-13,14-dihydro-;
cis-4,5-Didehydro-16,16-dimethyl-13,14-dihydro-;
cis-4,5-Didehydro-16-fluoro-13,14-dihydro-;
cis-4,5-Didehydro-16,16-difluoro-13,14-dihydro-;
cis-4,5-Didehydro-17-phenyl-18,19,20-trinor-13,14-dihydro-;
cis-4,5-Didehydro-17-(m-trifluoromethylphenyl)-18,19,20-trinor-13,14-dihydro-;
cis-4,5-Didehydro-17-(m-chlorophenyl)-18,19,20-trinor-13,14-dihydro-;
cis-4,5-Didehydro-17-(p-fluorophenyl)-18,19,20-trinor-13,14-dihydro-;
cis-4,5-Didehydro-16-methyl-17-phenyl-18,19,20-trinor-13,14-dihydro-;
cis-4,5-Didehydro-16,16-dimethyl-17-phenyl-18,19,20-trinor-13,14-dihydro-;
cis-4,5-Didehydro-16-fluoro-17-phenyl-18,19,20-trinor-13,14-dihydro-;
cis-4,5-Didehydro-16,16-difluoro-17-phenyl-18,19,20-trinor-13,14-dihydro-;
cis-4,5-Didehydro-16-phenyl-17,18,19,20-tetranor-13,14-dihydro-;
cis-4,5-Didehydro-16-(m-trifluoromethylphenyl)-17,18,19,20-tetranor-13,14-dihydro-;
cis-4,5-Didehydro-16-(m-chlorophenyl)-17,18,19,20-tetranor-13,14-dihydro-;
cis-4,5-Didehydro-16-(p-fluorophenyl)-17,18,19,20-tetranor-13,14-dihydro-;
cis-4,5-Didehydro-16-phenyl-18,19,20-trinor-13,14-dihydro-;
cis-4,5-Didehydro-16-methyl-16-phenyl-18,19,20-trinor-13,14-dihydro-;
cis-4,5-Didehydro-16-phenoxy-17,18,19,20-tetranor-13,14-dihydro-;
cis-4,5-Didehydro-16-(m-trifluoromethylphenoxy)-17,18,19,20-tetranor-13,14-dihydro-;
cis-4,5-Didehydro-16-(m-chlorophenoxy)-17,18,19,20-tetranor-13,14-dihydro-;
cis-4,5-Didehydro-16-(p-fluorophenoxy)-17,18,19,20-tetranor-13,14-dihydro-;
cis-4,5-Didehydro-16-methyl-16-phenoxy-18,19,20-trinor-13,14-dihydro-;
cis-4,5-Didehydro-15-epi-13-cis-;
cis-4,5-Didehydro-15-methyl-15-epi-13-cis-;
cis-4,5-Didehydro-16-methyl-15-epi-13-cis-;
cis-4,5-Didehydro-16,16-dimethyl-15-epi-13-cis-;
cis-4,5-Didehydro-16-fluoro-15-epi-13-cis-;
cis-4,5-Didehydro-16,16-difluoro-15-epi-13-cis-;
cis-4,5-Didehydro-17-phenyl-18,19,20-trinor-15-epi-13-cis-;
cis-4,5-Didehydro-17-(m-trifluoromethylphenyl)-18,19,20-trinor-15-epi-13-cis-;
cis-4,5-Didehydro-17-(m-chlorophenyl)-18,19,20-trinor-15-epi-13-cis-;
cis-4,5-Didehydro-17-(p-fluorophenyl)-18,19,20-trinor-15-epi-13-cis-;
cis-4,5-Didehydro-16-methyl-17-phenyl-18,19,20-trinor-15-epi-13-cis-;
cis-4,5-Didehydro-16,16-dimethyl-17-phenyl-18,19,20-trinor-15-epi-13-cis-;
cis-4,5-Didehydro-16-fluoro-17-phenyl-18,19,20-trinor-15-epi-13-cis-;
cis-4,5-Didehydro-16,16-difluoro-17-phenyl-18,19,20-trinor-15-epi-13-cis-;
cis-4,5-Didehydro-16-phenyl-17,18,19,20-tetranor-15-epi-13-cis-;
cis-4,5-Didehydro-16-(m-trifluoromethylphenyl)-17,18,19,20-tetranor-15-epi-13-cis-;
cis-4,5-Didehydro-16-(m-chlorophenyl)-17,18,19,20-tetranor-15-epi-13-cis-;
cis-4,5-Didehydro-16-(p-fluorophenyl)-17,18,19,20-tetranor-15-epi-13-cis-;
cis-4,5-Didehydro-16-phenyl-18,19,20-trinor-15-epi-13-cis-;
cis-4,5-Didehydro-16-methyl-16-phenyl-18,19,20-tetranor-15-epi-13-cis-;
cis-4,5-Didehydro-16-phenoxy-17,18,19,20-tetranor-15-epi-13-cis-;
cis-4,5-Didehydro-16-(m-trifluoromethylphenoxy)-17,18,19,20-tetranor-15-epi-13-cis-;
cis-4,5-Didehydro-16-(m-chlorophenoxy)-17,18,19,20-tetranor-15-epi-13-cis-;
cis-4,5-Didehydro-16-(p-fluorophenoxy)-17,18,19,20-tetranor-15-epi-13-cis-;
cis-4,5-Didehydro-16-phenoxy-18,19,20-trinor-15-epi-13-cis-;
cis-4,5-Didehydro-16-methyl-16-phenoxy-18,19,20-trinor-15-epi-13-cis-;
2,2-Difluoro-;
2,2-Difluoro-15-methyl-;

2,2-Difluoro-16-methyl-;
2,2-Difluoro-16,16-dimethyl-;
2,2,16-Trifluoro-;
2,2,16,16-Tetrafluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2,16-Trifluoro-17-phenyl-18,19,20-trinor-;
2,2,16,16-Tetrafluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,18,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-15-methyl-13,14-didehydro-;
2,2-Difluoro-16-methyl-13,14-didehydro-;
2,2-Difluoro-16,16-dimethyl-13,14-didehydro-;
2,2,16-Trifluoro-13,14-didehydro-;
2,2,16,16-Tetrafluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-(p-fluorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-(p-fluorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-15-methyl-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Dihydro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14,-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-methyl-16-phenoxy-18,19,20-trinor-13,14-dihydro-;
2,2-Difluoro-15-epi-13-cis-;
2,2-Difluoro-15-methyl-15-epi-13-cis-;
2,2-Difluoro-16-methyl-15-epi-13-cis-;
2,2-Difluoro-16,16-dimethyl-15-epi-13-cis-;
2,2,16-Trifluoro-15-epi-13-cis-;
2,2,16,16-Tetrafluoro-15-epi-13-cis-;
2,2-Difluoro-17-phenyl-18,19,20-trinor-15-epi-13-cis-;
2,2-Difluoro-17-(m-trifluoromethylphenyl)-18,19,20-trinor-15-epi-13-cis-;
2,2-Difluoro-17-(m-chlorophenyl)-18,19,20-trinor-15-epi-13-cis-;
2,2-Difluoro-17-(p-fluorophenyl)-18,19,20-trinor-15-epi-13-cis-;
2,2-Difluoro-16-methyl-17-phenyl-18,19,20-trinor-15-epi-13-cis-;
2,2-Difluoro-16,16-dimethyl-17-phenyl-18,19,20-trinor-15-epi-13-cis-;

2,2,16-Trifluoro-17-phenyl-18,19,20-trinor-15-epi-13-cis-;
2,2,16,16-Tetrafluoro-17-phenyl-18,19,20-trinor-15-epi-13-cis-;
2,2-Difluoro-16-phenyl-17,18,19,20-tetranor-15-epi-13-cis-;
2,2-Difluoro-16-(m-trifluoromethylphenyl)-17,18,19,20-tetranor-15-epi-13-cis-;
2,2-Difluoro-16-(m-chlorophenyl)-17,18,19,20-tetranor-15-epi-13-cis-;
2,2-Difluoro-16-(p-fluorophenyl)-17,18,19,20-tetranor-15-epi-13-cis-;
2,2-Difluoro-16-phenyl-18,19,20-trinor-15-epi-13-cis-;
2,2-Difluoro-16-methyl-16-phenyl-18,19,20-trinor-15-epi-13-cis-;
2,2-Difluoro-16-phenoxy-17,18,19,20-tetranor-15-epi-13-cis-;
2,2-Difluoro-16-(m-trifluoromethylphenoxy)-17,18,19,20-tetranor-15-epi-13-cis-;
2,2-Difluoro-16-(m-chlorophenoxy)-17,18,19,20-tetranor-15-epi-13-cis-;
2,2-Difluoro-16-(p-fluorophenoxy)-17,18,19,20-tetranor-15-epi-13-cis-;
2,2-Difluoro-16-phenoxy-18,19,20-trinor-15-epi-13-cis-;
2,2-Difluoro-16-methyl-16-phenoxy-18,19,20-trinor-15-epi-13-cis-;
5-Oxa-;
5-Oxa-15-methyl-;
5-Oxa-16-methyl-;
5-Oxa-16,16-dimethyl-;
5-Oxa-16-fluoro-;
5-Oxa-16,16-difluoro-;
5-Oxa-17-phenyl-18,19,20-trinor-;
5-Oxa-17-(m-trifluoromethylphenyl)-18,19,20-trinor-;
5-Oxa-17-(m-chlorophenyl)-18,19,20-trinor-;
5-Oxa-17-(p-fluorophenyl)-18,19,20-trinor-;
5-Oxa-16-methyl-17-phenyl-18,19,20-trinor-;
5-Oxa-16,16-dimethyl-17-phenyl-18,19,20-trinor-;
5-Oxa-16-fluoro-17-phenyl-18,19,20-trinor-;
5-Oxa-16,16-difluoro-17-phenyl-18,19,20-trinor-;
5-Oxa-16-phenyl-17,18,19,20-tetranor-;
5-Oxa-16-(m-trifluoromethylphenyl)-17,18,19,20-tetranor-;
5-Oxa-16-(m-chlorophenyl)-17,18,19,20-tetranor-;
5-Oxa-16-(p-fluorophenyl)-17,18,19,20-tetranor-;
5-Oxa-16-phenyl-18,19,20-trinor-;
5-Oxa-16-methyl-16-phenyl-18,19,20-trinor-;
5-Oxa-16-phenoxy-17,18,19,20-tetranor-;
5-Oxa-16-(m-trifluoromethylphenoxy)-17,18,19,20-tetranor-;
5-Oxa-16-(m-chlorophenoxy)-17,18,19,20-tetranor-;
5-Oxa-16-(p-fluorophenoxy)-17,18,19,20-tetranor-;
5-Oxa-16-phenoxy-18,19,20-trinor-;
5-Oxa-16-methyl-16-phenoxy-18,19,20-trinor-;
5-Oxa-15-methyl-13,14-didehydro-;
5-Oxa-16-methyl-13,14-didehydro-;
5-Oxa-16,16-dimethyl-13,14-didehydro-;
5-Oxa-16-fluoro-13,14-didehydro-;
5-Oxa-16,16-difluoro-13,14-didehydro-;
5-Oxa-17-phenyl-18,19,20-trinor-13,14-didehydro-;
5-Oxa-17-(m-trifluoromethylphenyl)-18,19,20-trinor-13,14-didehydro-;
5-Oxa-17-(m-chlorophenyl)-18,19,20-trinor-13,14-didehydro-;
5-Oxa-17-(p-fluorophenyl)-18,19,20-trinor-13,14-didehydro-;
5-Oxa-16-methyl-17-phenyl-18,19,20-trinor-13,14-didehydro-;
5-Oxa-16,16-dimethyl-17-phenyl-18,19,20-trinor-13,14-didehydro-;
5-Oxa-16-fluoro-17-phenyl-18,19,20-trinor-13,14-didehydro-;
5-Oxa-16,16-difluoro-17-phenyl-18,19,20-trinor-13,14-didehydro-;
5-Oxa-16-phenyl-17,18,19,20-tetranor-13,14-didehydro-;
5-Oxa-16-(m-trifluoromethylphenyl)-17,18,19,20-tetranor-13,14-didehydro-;
5-Oxa-16-(m-chlorophenyl)-17,18,19,20-tetranor-13,14-didehydro-;
5-Oxa-16-(p-fluorophenyl)-17,18,19,20-tetranor-13,14-didehydro-;
5-Oxa-16-phenyl-18,19,20-trinor-13,14-didehydro-;
5-Oxa-16-methyl-16-phenyl-18,19,20-trinor-13,14-didehydro-;
5-Oxa-16-phenoxy-17,18,19,20-tetranor-13,14-didehydro-;
5-Oxa-16-(m-trifluoromethylphenoxy)-17,18,19,20-tetranor-13,14-didehydro-;
5-Oxa-16-(m-chlorophenoxy)-17,18,19,20-tetranor-13,14-didehydro-;
5-Oxa-16-(p-fluorophenoxy)-17,18,19,20-tetranor-13,14-didehydro-;
5-Oxa-16-phenoxy-18,19,20-trinor-13,14-didehydro-;
5-Oxa-16-methyl-16-phenoxy-18,19,20-trinor-13,14-didehydro-;
5-Oxa-13,14-dihydro-;
5-Oxa-15-methyl-13,14-dihydro-;
5-Oxa-16-methyl-13,14-dihydro-;
5-Oxa-16,16-dimethyl-13,14-dihydro-;
5-Oxa-16-fluoro-13,14-dihydro-;
5-Oxa-16,16-difluoro-13,14-dihydro-;
5-Oxa-17-phenyl-18,19,20-trinor-13,14-dihydro-;
5-Oxa-17-(m-trifluoromethylphenyl)-18,19,20-trinor-13,14-dihydro-;
5-Oxa-17-(m-chlorophenyl)-18,19,20-trinor-13,14-dihydro-;
5-Oxa-17-(p-fluorophenyl)-18,19,20-trinor-13,14-dihydro-;
5-Oxa-16-methyl-17-phenyl-18,19,20-trinor-13,14-dihydro-;
5-Oxa-16,16-dimethyl-17-phenyl-18,19,20-trinor-13,14-dihydro-;
5-Oxa-16-fluoro-17-phenyl-18,19,20-trinor-13,14-dihydro-;
5-Oxa-16,16-difluoro-17-phenyl-18,19,20-trinor-13,14-dihydro-;
5-Oxa-16-phenyl-17,18,19,20-tetranor-13,14-dihydro-;
5-Oxa-16-(m-trifluoromethylphenyl)-17,18,19,20-tetranor-13,14-dihydro-;
5-Oxa-16-(m-chlorophenyl)-17,18,19,20-tetranor-13,14-dihydro-;
5-Oxa-16-(p-fluorophenyl)-17,18,19,20-tetranor-13,14-dihydro-;
5-Oxa-16-phenyl-18,19,20-trinor-13,14-dihydro-;
5-Oxa-16-methyl-16-phenyl-18,19,20-trinor-13,14-dihydro-;
5-Oxa-16-phenoxy-17,18,19,20-tetranor-13,14-dihydro-;
5-Oxa-16-(m-trifluoromethylphenoxy)-17,18,19,20-tetranor-13,14-dihydro-;
5-Oxa-16-(m-chlorophenoxy)-17,18,19,20-tetranor-13,14-dihydro-;
5-Oxa-16-(p-fluorophenoxy)-17,18,19,20-tetranor-13,14-dihydro-;
5-Oxa-16-methyl-16-phenoxy-18,19,20-trinor-13,14-dihydro-;

5-Oxa-15-epi-13-cis-;
5-Oxa-15-methyl-15-epi-13-cis-;
5-Oxa-16-methyl-15-epi-13-cis-;
5-Oxa-16,16-dimethyl-15-epi-13-cis-;
5-Oxa-16-fluoro-15-epi-13-cis-;
5-Oxa-16,16-difluoro-15-epi-13-cis-;
5-Oxa-17-phenyl-18,19,20-trinor-15-epi-13-cis-;
5-Oxa-17-(m-trifluoromethylphenyl)-18,19,20-trinor-15-epi-13-cis-;
5-Oxa-17-(m-chlorophenyl)-18,19,20-trinor-15-epi-13-cis-;
5-Oxa-17-(p-fluorophenyl)-18,19,20-trinor-15-epi-13-cis-;
5-Oxa-16-methyl-17-phenyl-18,19,20-trinor-15-epi-13-cis-;
5-Oxa-16,16-dimethyl-17-phenyl-18,19,20-trinor-15-epi-13-cis-;
5-Oxa-16-fluoro-17-phenyl-18,19,20-trinor-15-epi-13-cis-;
5-Oxa-16,16-difluoro-17-phenyl-18,19,20-trinor-15-epi-13-cis-;
5-Oxa-16-phenyl-17,18,19,20-tetranor-15-epi-13-cis-;
5-Oxa-16-(m-trifluoromethylphenyl)-17,18,19,20-tetranor-15-epi-13-cis-;
5-Oxa-16-(m-chlorophenyl)-17,18,19,20-tetranor-15-epi-13-cis-;
5-Oxa-16-(p-fluorophenyl)-17,18,19,20-tetranor-15-epi-13-cis-;
5-Oxa-16-phenyl-18,19,20-trinor-15-epi-13-cis-;
5-Oxa-16-methyl-16-phenyl-18,19,20-trinor-15-epi-13-cis-;
5-Oxa-16-phenoxy-17,18,19,20-tetranor-15-epi-13-cis-;
5-Oxa-16-(m-trifluoromethylphenoxy)-17,18,19,20-tetranor-15-epi-13-cis-;
5-Oxa-16-(m-chlorophenoxy)-17,18,19,20-tetranor-15-epi-13-cis-;
5-Oxa-16-(p-fluorophenoxy)-17,18,19,20-tetranor-15-epi-13-cis-;
5-Oxa-16-phenoxy-18,19,20-trinor-15-epi-13-cis-;
5-Oxa-16-methyl-16-phenoxy-18,19,20-trinor-15-epi-13-cis-;
4-Oxa-;
4-Oxa-15-methyl-;
4-Oxa-16-methyl-;
4-Oxa-16,16-dimethyl-;
4-Oxa-16-fluoro-;
4-Oxa-16,16-difluoro-;
4-Oxa-17-phenyl-18,19,20-trinor-;
4-Oxa-17-(m-trifluoromethylphenyl)-18,19,20-trinor-;
4-Oxa-17-(m-chlorophenyl)-18,19,20-trinor-;
4-Oxa-17-(p-fluorophenyl)-18,19,20-trinor-;
4-Oxa-16-methyl-17-phenyl-18,19,20-trinor-;
4-Oxa-16,16-dimethyl-17-phenyl-18,19,20-trinor-;
4-Oxa-16-fluoro-17-phenyl-18,19,20-trinor-;
4-Oxa-16,16-difluoro-17-phenyl-18,19,20-trinor-;
4-Oxa-16-phenyl-17,18,19,20-tetranor-;
4-Oxa-16-(m-trifluoromethylphenyl)-17,18,19,20-tetranor-;
4-Oxa-16-(m-chlorophenyl)-17,18,19,20-tetranor-;
4-Oxa-16-(p-fluorophenyl)-17,18,19,20-tetranor-;
4-Oxa-16-phenyl-18,19,20-trinor-;
4-Oxa-16-methyl-16-phenyl-18,19,20-trinor-;
4-Oxa-16-phenoxy-17,18,19,20-tetranor-;
4-Oxa-16-(m-trifluoromethylphenoxy)-17,18,19,20-tetranor-;
4-Oxa-16-(m-chlorophenoxy)-17,18,19,20-tetranor-;
4-Oxa-16-(p-fluorophenoxy)-17,18,18,20-tetranor-;
4-Oxa-16-phenoxy-18,19,20-trinor-;
4-Oxa-16-methyl-16-phenoxy-18,19,20-trinor-;
4-Oxa-15-methyl-13,14-didehydro-;
4-Oxa-16-methyl-13,14-didehydro-;
4-Oxa-16,16-dimethyl-13,14-didehydro-;
4-Oxa-16-fluoro-13,14-didehydro-;
4-Oxa-16,16-difluoro-13,14-didehydro-;
4-Oxa-17-phenyl-18,19,20-trinor-13,14-didehydro-;
4-Oxa-17-(m-trifluoromethylphenyl)-18,19,20-trinor-13,14-didehydro-;
4-Oxa-17-(m-chlorophenyl)-18,19,20-trinor-13,14-didehydro-;
4-Oxa-17-(p-fluorophenyl)-18,19,20-trinor-13,14-didehydro-;
4-Oxa-16-methyl-17-phenyl-18,19,20-trinor-13,14-didehydro-;
4-Oxa-16,16-dimethyl-17-phenyl-18,19,20-trinor-13,14-didehydro-;
4-Oxa-16-fluoro-17-phenyl-18,19,20-trinor-13,14-didehydro-;
4-Oxa-16,16-difluoro-17-phenyl-18,19,20-trinor-13,14-didehydro-;
4-Oxa-16-phenyl-17,18,19,20-tetranor-13,14-didehydro-;
4-Oxa-16-(m-trifluoromethylphenyl)-17,18,19,20-tetranor-13,14-didehydro-;
4-Oxa-16-(m-chlorophenyl)-17,18,19,20-tetranor-13,14-didehydro-;
4-Oxa-16-(p-fluorophenyl)-17,18,19,20-tetranor-13,14-didehydro-;
4-Oxa-16-phenyl-18,19,20-trinor-13,14-didehydro-;
4-Oxa-16-methyl-16-phenyl-18,19,20-trinor-13,14-didehydro-;
4-Oxa-16-phenoxy-17,18,19,20-tetranor-13,14-didehydro-;
4-Oxa-16-(m-trifluoromethylphenoxy)-17,18,19,20-tetranor-13,14-didehydro-;
4-Oxa-16-(m-chlorophenoxy)-17,18,19,20-tetranor-13,14-didehydro-;
4-Oxa-16-(p-fluorophenoxy)-17,18,19,20-tetranor-13,14-didehydro-;
4-Oxa-16-phenoxy-18,19,20-trinor-13,14-didehydro-;
4-Oxa-16-methyl-16-phenoxy-18,19,20-trinor-13,14-didehydro-;
4-Oxa-13,14-dihydro-;
4-Oxa-15-methyl-13,14-dihydro-;
4-Oxa-16-methyl-13,14-dihydro-;
4-Oxa-16,16-dimethyl-13,14-dihydro-;
4-Oxa-16-fluoro-13,14-dihydro-;
4-Oxa-16,16-difluoro-13,14-dihydro-;
4-Oxa-17-phenyl-18,19,20-trinor-13,14-dihydro-;
4-Oxa-17-(m-trifluoromethylphenyl)-18,19,20-trinor-13,14-dihydro-;
4-Oxa-17-(m-chlorophenyl)-18,19,20-trinor-13,14-dihydro-;
4-Oxa-17-(p-fluorophenyl)-18,19,20-trinor-13,14-dihydro-;
4-Oxa-16-methyl-17-phenyl-18,19,20-trinor-13,14-dihydro-;
4-Oxa-16,16-dimethyl-17-phenyl-18,19,20-trinor-13,14-dihydro-;
4-Oxa-16-fluoro-17-phenyl-18,19,20-trinor-13,14-dihydro-;
4-Oxa-16,16-difluoro-17-phenyl-18,19,20-trinor-13,14-didhydro-;
4-Oxa-16-phenyl-17,18,19,20-tetranor-13,14-dihydro-;
4-Oxa-16-(m-trifluoromethylphenyl)-17,18,19,20-tetranor-13,14-dihydro-;

4-Oxa-16-(m-chlorophenyl)-17,18,19,20-tetranor-13,14-dihydro-;
4-Oxa-16-(p-fluorophenyl)-17,18,19,20-tetranor-13,14-dihydro-;
4-Oxa-16-phenyl-18,19,20-trinor-13,14-dihydro-;
4-Oxa-16-methyl-16-phenyl-18,19,20-trinor-13,14-dihydro-;
4-Oxa-16-phenoxy-17,18,19,20-tetranor-13,14dihydro-;
4-Oxa-16-(m-trifluoromethylphenoxy)-17,18,19,20-tetranor-13,14-dihydro-;
4-Oxa-16-(m-chlorophenoxy)-17,18,19,20-tetranor-13,14-dihydro-;
4-Oxa-16-(p-fluorophenoxy)-17,18,19,20-tetranor-13,14-dihydro-;
4-Oxa-16-methyl-16-phenoxy-18,19,20-trinor-13,14-dihydro-;
4-Oxa-15-epi-13-cis-;
4-Oxa-15-methyl-15-epi-13-cis-;
4-Oxa-16-methyl-15-epi-13-cis-;
4-Oxa-16,16-dimethyl-15-epi-13-cis-;
4-Oxa-16-fluoro-15-epi-13-cis-;
4-Oxa-16,16-difluoro-15-epi-13-cis-;
4-Oxa-17-phenyl-18,19,20-trinor-15-epi-13-cis-;
4-Oxa-17-(m-trifluoromethylphenyl)-18,19,20-trinor-15-epi-13-cis-;
4-Oxa-17-(m-chlorophenyl)-18,19,20-trinor-15-epi-13-cis-;
4-Oxa-17-(p-fluorophenyl)-18,19,20-trinor-15-epi-13-cis-;
4-Oxa-16-methyl-17-phenyl-18,19,20-trinor-15-epi-13-cis-;
4-Oxa-16,16-dimethyl-17-phenyl-18,19,20-trinor-15-epi-13-cis-;
4-Oxa-16-fluoro-17-phenyl-18,19,20-trinor-15-epi-13-cis-;
4-Oxa-16,16-difluoro-17-phenyl-18,19,20-trinor-15-epi-13-cis-;
4-Oxa-16-phenyl-17,18,19,20-tetranor-15-epi-13-cis-;
4-Oxa-16-(m-trifluoromethylphenyl)-17,18,19,20-tetranor-15-epi-13-cis-;
4-Oxa-16-(m-chlorophenyl)-17,18,19,20-tetranor-15-epi-13-cis-;
4-Oxa-16-(p-fluorophenyl)-17,18,19,20-tetranor-15-epi-13-cis-;
4-Oxa-16-phenyl-18,19,20-trinor-15-epi-13-cis-;
4-Oxa-16-methyl-16-phenyl-18,19,20-trinor-15-epi-13-cis-;
4-Oxa-16-phenoxy-17,18,19,20-tetranor-15-epi-13-cis-;
4-Oxa-16-(m-trifluoromethylphenoxy)-17,18,19,20-tetranor-15-epi-13-cis-;
4-Oxa-16-(m-chlorophenoxy)-17,18,19,20-tetranor-15-epi-13-cis-;
4-Oxa-16-(p-fluorophenoxy)-17,18,19,20-tetranor-15-epi-13-cis-;
4-Oxa-16-phenoxy-18,19,20-trinor-15-epi-13-cis-;
4-Oxa-16-methyl-16-phenoxy-18,19,20-trinor-15-epi-13-cis-;
3-Oxa-;
3-Oxa-15-methyl-;
3-Oxa-16-methyl-;
3-Oxa-16,16-dimethyl-;
3-Oxa-16-fluoro-;
3-Oxa-16,16-difluoro-;
3-Oxa-17-phenyl-18,19,20-trinor-;
3-Oxa-17-(m-trifluoromethylphenyl)-18,19,20-trinor-;
3-Oxa-17-(m-chlorophenyl)-18,19,20-trinor-;
3-Oxa-17-(p-fluorophenyl)-18,19,20-trinor-;
3-Oxa-16-methyl-17-phenyl-18,19,20-trinor-;
3-Oxa-16,16-dimethyl-17-phenyl-18,19,20-trinor-;
3-Oxa-16-fluoro-17-phenyl-18,19,20-trinor-;
3-Oxa-16,16-difluoro-17-phenyl-18,19,20-trinor-;
3-Oxa-16-phenyl-17,18,19,20-tetranor-;
3-Oxa-16-(m-trifluoromethylphenyl)-17,18,19,20-tetranor-;
3-Oxa-16-(m-chlorophenyl)-17,18,19,20-tetranor-;
3-Oxa-16-(p-fluorophenyl)-17,18,19,20-tetranor-;
3-Oxa-16-phenyl-18,19,20-trinor-;
3-Oxa-16-methyl-16-phenyl-18,19,20-trinor-;
3-Oxa-16-phenoxy-17,18,19,20-tetranor-;
3-Oxa-16-(m-trifluoromethylphenoxy)-17,18,19,20-tetranor-;
3-Oxa-16-(m-chlorophenoxy)-17,18,19,20-tetranor-;
3-Oxa-16-(p-fluorophenoxy)-17,18,19,20-tetranor-;
3-Oxa-16-phenoxy-18,19,20-trinor-;
3-Oxa-16-methyl-16-phenoxy-18,19,20-trinor-;
3-Oxa-15-methyl-13,14-didehydro-;
3-Oxa-16-methyl-13,14-didehydro-;
3-Oxa-16,16-dimethyl-13,14-didehydro-;
3-Oxa-16-fluoro-13,14-didehydro-;
3-Oxa-16,16-difluoro-13,14-didehydro-;
3-Oxa-17-phenyl-18,19,20-trinor-13,14-didehydro-;
3-Oxa-17-(m-trifluoromethylphenyl)-18,19,20-trinor-13,14-didehydro-;
3-Oxa-17-(m-chlorophenyl)-18,19,20-trinor-13,14-didehydro-;
3-Oxa-17-(p-fluorophenyl)-18,19,20-trinor-13,14-didehydro-;
3-Oxa-16-methyl-17-phenyl-18,19,20-trinor-13,14-didehydro-;
3-Oxa-16,16-dimethyl-17-phenyl-18,19,20-trinor-13,14-didehydro-;
3-Oxa-16-fluoro-17-phenyl-18,19,20-trinor-13,14-didehydro-;
3-Oxa-16,16-difluoro-17-phenyl-18,19,20-trinor-13,14-didehydro-;
3-Oxa-16-phenyl-17,18,19,20-tetranor-13,14-didehydro-;
3-Oxa-16-(m-trifluoromethylphenyl)-17,18,19,20-tetranor-13,14-didehydro-;
3-Oxa-16-(m-chlorophenyl)-17,18,19,20-tetranor-13,14-didehydro-;
3-Oxa-16-(p-fluorophenyl)-17,18,19,20-tetranor-13,14-didehydro-;
3-Oxa-16-phenyl-18,19,20-trinor-13,14-didehydro-;
3-Oxa-16-methyl-16-phenyl-18,19,20-trinor-13,14-didehydro-;
3-Oxa-16-phenoxy-17,18,19,20-tetranor-13,14-didehydro-;
3-Oxa-16-(m-trifluoromethylphenoxy)-17,18,19,20-tetranor-13,14-didehydro-;
3-Oxa-16-(m-chlorophenoxy)-17,18,19,20-tetranor-13,14-didehydro-;
3-Oxa-16-(p-fluorophenoxy)-17,18,19,20-tetranor-13,14-didehydro-;
3-Oxa-16-phenoxy-18,19,20-trinor-13,14-didehydro-;
3-Oxa-16-methyl-16-phenoxy-18,19,20-trinor-13,14-didehydro-;
3-Oxa-13,14-dihydro-;
3-Oxa-15-methyl-13,14-dihydro-;
3-Oxa-16-methyl-13,14-dihydro-;
3-Oxa-16,16-dimethyl-13,14-dihydro-;
3-Oxa-16-fluoro-13,14-dihydro-;
3-Oxa-16,16-difluoro-13,14-dihydro-;
3-Oxa-17-phenyl-18,19,20-trinor-13,14-dihydro-;
3-Oxa-17-(m-trifluoromethylphenyl)-18,19,20-trinor-13,14-dihydro-;

3-Oxa-17-(m-chlorophenyl)-18,19,20-trinor-13,14-dihydro-;
3-Oxa-17-(p-fluorophenyl)-18,19,20-trinor-13,14-dihydro-;
3-Oxa-16-methyl-17-phenyl-18,19,20-trinor-13,14-dihydro-;
3-Oxa-16,16-dimethyl-17-phenyl-18,19,20-trinor-13,14-dihydro-;
3-Oxa-16-fluoro-17-phenyl-18,19,20-trinor-13,14-dihydro-;
3-Oxa-16,16-difluoro-17-phenyl-18,19,20-trinor-13,14-dihydro-;
3-Oxa-16-phenyl-17,18,19,20-tetranor-13,14-dihydro-;
3-Oxa-16-(m-trifluoromethylphenyl)-17,18,19,20-tetranor-13,14-dihydro-;
3-Oxa-16-(m-chlorophenyl)-17,18,19,20-tetranor-13,14-dihydro-;
3-Oxa-16-(p-fluorophenyl)-17,18,19,20-tetranor-13,14-dihydro-;
3-Oxa-16-phenyl-18,19,20-trinor-13,14-dihydro-;
3-Oxa-16-methyl-16-phenyl-18,19,20-trinor-13,14-dihydro-;
3-Oxa-16-phenoxy-17,18,19,20-tetranor-13,14-dihydro-;
3-Oxa-16-(m-trifluoromethylphenoxy)-17,18,19,20-tetranor-13,14-dihydro-;
3-Oxa-16-(m-chlorophenoxy)-17,18,19,20-tetranor-13,14-dihydro-;
3-Oxa-16-(p-fluorophenoxy)-17,18,19,20-tetranor-13,14-dihydro-;
3-Oxa-16-methyl-16-phenoxy-18,19,20-trinor-13,14-dihydro-;
3-Oxa-15-epi-13-cis-;
3-Oxa-15-methyl-15-epi-13-cis-;
3-Oxa-16-methyl-15-epi-13-cis-;
3-Oxa-16,16-dimethyl-15-epi-13-cis-;
3-Oxa-16-fluoro-15-epi-13-cis-;
3-Oxa-16,16-difluoro-15-epi-13-cis-;
3-Oxa-17-phenyl-18,19,20-trinor-15-epi-13-cis-;
3-Oxa-17-(m-trifluoromethylphenyl)-18,19,20-trinor-15-epi-13-cis-;
3-Oxa-17-(m-chlorophenyl)-18,19,20-trinor-15-epi-13-cis-;
3-Oxa-17-(p-fluorophenyl)-18,19,20-trinor-15-epi-13-cis-;
3-Oxa-16-methyl-17-phenyl-18,19,20-trinor-15-epi-13-cis-;
3-Oxa-16,16-dimethyl-17-phenyl-18,19,20-trinor-15-epi-13-cis-;
3-Oxa-16-fluoro-17-phenyl-18,19,20-trinor-15-epi-13-cis-;
3-Oxa-16,16-difluoro-17-phenyl-18,19,20-trinor-15-epi-13-cis-;
3-Oxa-16-phenyl-17,18,19,20-tetranor-15-epi-13-cis-;
3-Oxa-16-(m-trifluoromethylphenyl)-17,18,19,20-tetranor-15-epi-13-cis-;
3-Oxa-16-(m-chlorophenyl)-17,18,19,20-tetranor-15-epi-13-cis-;
3-Oxa-16-(p-fluorophenyl)-17,18,19,20-tetranor-15-epi-13-cis-;
3-Oxa-16-phenyl-18,19,20-trinor-15-epi-13-cis-;
3-Oxa-16-methyl-16-phenyl-18,19,20-trinor-15-epi-13-cis-;
3-Oxa-16-phenoxy-17,18,19,20-tetranor-15-epi-13-cis-;
3-Oxa-16-(m-trifluoromethylphenoxy)-17,18,19,20-tetranor-15-epi-13-cis-;
3-Oxa-16-(m-chlorophenoxy)-17,18,19,20-tetranor-15-epi-13-cis-;
3-Oxa-16-(p-fluorophenoxy)-17,18,19,20-tetranor-15-epi-13-cis-;
3-Oxa-16-phenoxy-18,19,20-trinor-15-epi-13-cis-;
3-Oxa-16-methyl-16-phenoxy-18,19,20-trinor-15-epi-13-cis-;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-17-phenyl-18,19,20-trinor-;
trans-2,3-Didehydro-17-(m-trifluoromethylphenyl)-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3-Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-Didehydro-16-phenyl-18,19,20-trinor-;
trans-2,3-Didehydro-16-methyl-16-phenoxy-18,19,20-trinor-;
trans-2,3-Didehydro-15-methyl-13,14-didehydro-;
trans-2,3-Didehydro-16-methyl-13,14-didehydro-;
trans-2,3-Didehydro-16,16-dimethyl-13,14-didehydro-;
trans-2,3-Didehydro-16-fluoro-13,14-didehydro-;
trans-2,3-Didehydro-16,16-difluoro-13,14-didehydro-;
trans-2,3-Didehydro-17-phenyl-18,19,20-trinor-13,14-didehydro-;
trans-2,3-Didehydro-17-(m-trifluoromethylphenyl)-18,19,20-trinor-13,14-didehydro-;
trans-2,3-Didehydro-17-(m-chlorophenyl)-18,19,20-trinor-13,14-didehydro-;
trans-2,3-Didehydro-17-(p-fluorophenyl)-18,19,20-trinor-13,14-didehydro-;
trans-2,3-Didehydro-16-methyl-17-phenyl-18,19,20-trinor-13,14-didehydro-;
trans-2,3-Didehydro-16,16-dimethyl-17-phenyl-18,19,20-trinor-13,14-didehydro-;
trans-2,3-Didehydro-16-fluoro-17-phenyl-18,19,20-trinor-13,14-didehydro-;
trans-2,3-Didehydro-16,16-difluoro-17-phenyl-18,19,20-trinor-13,14-didehydro;

trans-2,3-Didehydro-16-phenyl-17,18,19,20-tetranor-13,14-didehydro-;
trans-2,3-Didehydro-16-(m-trifluoromethylphenyl)-17,18,19,20-tetranor-13,14-didehydro-;
trans-2,3-Didehydro-16-(m-chlorophenyl)-17,18,19,20-tetranor-13,14-didehydro-;
trans-2,3-Didehydro-16-(p-fluorophenyl)-17,18,19,20-tetranor-13,14-didehydro-;
trans-2,3-Didehydro-16-phenyl-18,19,20-trinor-13,14-didehydro-;
trans-2,3-Didehydro-16-methyl-16-phenyl-18,19,20-trinor-13,14-didehydro-;
trans-2,3-Didehydro-16-phenoxy-17,18,19,20-tetranor-13,14-didehydro-;
trans-2,3-Didehydro-16-(m-trifluoromethylphenoxy)-17,18,19,20-tetranor-13,14-didehydro-;
trans-2,3-Didehydro-16-(m-chlorophenoxy)-17,18,19,20-tetranor-13,14-didehydro-;
trans-2,3-Didehydro-16-(p-fluorophenoxy)-17,18,19,20-tetranor-13,14-didehydro-;
trans-2,3-Didehydro-16-phenoxy-18,19,20-trinor-13,14-didehydro-;
trans-2,3-Didehydro-16-methyl-16-phenoxy-18,19,20-trinor-13,14-didehydro;
trans-2,3-Didehydro-13,14-dihydro-;
trans-2,3-Didehydro-15-methyl-13,14-dihydro-;
trans-2,3-Didehydro-16-methyl-13,14-dihydro-;
trans-2,3-Didehydro-16,16-dimethyl-13,14-dihydro-;
trans-2,3-Didehydro-16-fluoro-13,14-dihydro-;
trans-2,3-Didehydro-16,16-fluoro-13,14-dihydro-;
trans-2,3-Didehydro-17-phenyl-18,19,20-trinor-13,14-dihydro-;
trans-2,3-Didehydro-17-(m-trifluoromethylphenyl)-18,19,20-trinor-13,14-dihydro-;
trans-2,3-Didehydro-17-(m-chlorophenyl)-18,19,20-trinor-13,14-dihydro-;
trans-2,3-Didehydro-17-(p-fluorophenyl)-18,19,20-trinor-13,14-dihydro-;
trans-2,3-Didehydro-16-methyl-17-phenyl-18,19,20-trinor-13,14-dihydro-;
trans-2,3-Didehydro-16,16-dimethyl-17-phenyl-18,19,20-trinor-13,14-dihydro-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro-16-(m-trifluoromethylphenyl)-17,18,19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20-tetranor-13,14-dihydro-;
trans-2,3-Didehydro-16-(p-fluorophenoxy)-17,18,19,20-tetranor-13,14-dihydro-;
trans-2,3-Didehydro-16-methyl-16-phenoxy-18,19,20-trinor-13,14-dihydro-;
trans-2,3-Didehydro-15-epi-13-cis-;
trans-2,3-Didehydro-15-methyl-15-epi-13-cis-;
trans-2,3-Didehydro-16-methyl-15-epi-13-cis-;
trans-2,3-Didehydro-16,16-dimethyl-15-epi-13-cis-;
trans-2,3-Didehydro-16-fluoro-15-epi-13-cis-;
trans-2,3-Didehydro-16,16-difluoro-15-epi-13-cis-;
trans-2,3-Didehydro-17-phenyl-18,19,20-trinor-15-epi-13-cis-;
trans-2,3-Didehydro-17-(m-trifluoromethylphenyl)-18,19,20-trinor-15-epi-13-cis-;
trans-2,3-Didehydro-17-(m-chlorophenyl)-18,19,20-trinor-15-epi-13-cis-;
trans-2,3-Didehydro-17-(p-fluorophenyl)-18,19,20-trinor-15-epi-13-cis-;
trans-2,3-Didehydro-16-methyl-17-phenyl-18,19,20-trinor-15-epi-13-cis-;
trans-2,3-Didehydro-16,16-dimethyl-17-phenyl-18,19,20-trinor-15-epi-13-cis-;
trans-2,3-Didehydro-16-fluoro-17-phenol-18,19,20-trinor-15-epi-13-cis-;
trans-2,3-Didehydro-16,16-difluoro-17-phenyl-18,19,20-trinor-15-epi-13-cis-;
trans-2,3-Didehydro-16-phenyl-17,18,19,20-tetranor-15-epi-13-cis-;
trans-2,3-Didehydro-16-(m-trifluoromethylphenyl)-17,18,19,20-tetranor-15-epi-13-cis-;
trans-2,3-Didehydro-16-(m-chlorophenyl)-17,18,19,20-tetranor-15-epi-13-cis-;
trans-2,3-Didehydro-16-(p-fluorophenyl)-17,18,19,20-tetranor-15-epi-13-cis-;
trans-2,3-Didehydro-16-phenyl-18,19,20-trinor-15-epi-13-cis-;
trans-2,3-Didehydro-16-methyl-16-phenyl-18,19,20-trinor-15-epi-13-cis-;
trans-2,3-Didehydro-16-phenoxy-17,18,19,20-tetranor-15-epi-13-cis-;
trans-2,3-Didehydro-16-(m-trifluoromethylphenoxy)-17,18,19,20-tetranor-15-epi-13-cis-;
trans-2,3-Didehydro-16-(m-chlorophenoxy)-17,18,19,20-tetranor-15-epi-13-cis-;
trans-2,3-Didehydro-16-(p-fluorophenoxy)-17,18,19,20-tetranor-15-epi-13-cis-;
trans-2,3-Didehydro-16-phenoxy-18,19,20-trinor-15-epi-13-cis-;
trans-2,3-Didehydro-16-methyl-16-phenoxy-18,19,20-trinor-15-epi-13-cis-;
3,7-Inter-m-phenylene-4,5,6-trinor-;
3,7-Inter-m-phenylene-4,5,6-trinor-15-methyl-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,19,20-hexanor-;
3,7-Inter-m-phenylene-17-(p-fluorophenyl)-4,5,6,18,19,20-hexanor-;
3,7-Inter-m-phenylene-16-methyl-17-phenyl-4,5,6,18,19,20-hexanor-;
3,7-Inter-m-phenylene-16,16-dimethyl-17-phenyl-4,5,6,18,19,20-hexanor-;
3,7-Inter-m-phenylene-16-fluoro-17-phenyl-4,5,6,18,19,20-hexanor-;
3,7-Inter-m-phenylene-16,16-difluoro-17-phenyl-4,5,6,18,19,20-hexanor-;

3,7-Inter-m-phenylene-16-phenyl-4,5,6,17,18,19,20-heptanor-;
3,7-Inter-m-phenylene-16-(m-trifluoromethylphenyl)-4,5,6,17,18,19,20-heptanor-;
3,7-Inter-m-phenylene-16-(m-chlorophenyl)-4,5,6,17,18,19,20-heptanor-;
3,7-Inter-m-phenylene-16-(p-fluorophenyl)-4,5,6,17,18,19,20-heptanor-;
3,7-Inter-m-phenylene-16-phenyl-4,5,6,18,19,20-hexanor;
3,7-Inter-m-phenylene-16-methyl-16-phenyl-4,5,6,18,19,20-hexanor-;
3,7-inter-m-phenylene-16-phenoxy-4,5,6,17,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,17,18,19,20-heptanor-;
3,7-Inter-m-phenylene-16-(p-fluorophenoxy)-4,5,6,17,18,19,20-heptanor-;
3,7-Inter-m-phenylene-16-phenoxy-4,5,6,18,19,20-hexanor-;
3,7-Inter-m-phenylene-16-methyl-16-phenoxy-4,5,6,18,19,20-hexanor-;
3,7-Inter-m-phenylene-15-methyl-13,14-didehydro-4,5,6-trinor-;
3,7-Inter-m-phenylene-16-methyl-13,14-didehydro-4,5,6-trinor-;
3,7-Inter-m-phenylene-16,16-dimethyl-13,14-didehydro-4,5,6-trinor-;
3,7-Inter-m-phenylene-16-fluoro-13,14-didehydro-4,5,6-trinor-;
3,7-Inter-m-phenylene-16,16-difluoro-13,14-didehydro-4,5,6-trinor-;
3,7-Inter-m-phenylene-17-phenyl-4,5,6,18,19,20-hexanor-13,14-didehydro-;
3,7-Inter-m-phenylene-17-(m-trifluoromethylphenyl)-4,5,6,18,19,20-hexanor-13,14-didehydro-;
3,7-Inter-m-phenylene-17-(m-chlorophenyl)-4,5,6,18,19,20-hexanor-13,14-didehydro-;
3,7-Inter-m-phenylene-17-(p-fluorophenyl)-4,5,6,18,19,20-hexanor-13,14-didehydro-;
3,7-Inter-m-phenylene-16-methyl-17-phenyl-4,5,6,18,19,20-hexanor-13,14-didehydro-;
3,7-Inter-m-phenylene-16,16-dimethyl-17-phenyl-4,5,6,18,19,20-hexanor-13,14-didehydro-;
3,7-Inter-m-phenylene-16-fluoro-17-phenyl-4,5,6,18,19,20-hexanor-13,14-didehydro-;
3,7-Inter-m-phenylene-16,16-difluoro-17-phenyl-4,5,6,18,19,20-hexanor-13,14-didehydro-;
3,7-Inter-m-phenylene-16-phenyl-4,5,6,17,18,19,20-heptanor-13,14-didehydro-;
3,7-Inter-m-phenylene-16-(m-trifluoromethylphenyl)-4,5,6,17,18,19,20-heptanor-13,14-didehydro-;
3,7-Inter-m-phenylene-16-(m-chlorophenyl)-4,5,6,17,18,19,20-heptanor-13,14-didehydro-;
3,7-Inter-m-phenylene-16-(p-fluorophenyl)-4,5,6,17,18,19,20-heptanor-13,14-didehydro-;
3,7-Inter-m-phenylene-16-phenyl-4,5,6,18,19,20-hexanor-13,14-didehydro-;
3,7-Inter-m-phenylene-16-methyl-16-phenyl-4,5,6,18,19,20-hexanor-13,14-didehydro-;
3,7-Inter-m-phenylene-16-phenoxy-4,5,6,17,18,19,20-heptanor-13,14-didehydro-;
3,7-Inter-m-phenylene-16-(m-trifluoromethylphenoxy)-4,5,6,17,18,19,20-heptanor-13,14-didehydro-;
3,7-Inter-m-phenylene-16-(m-chlorophenoxy)-4,5,6,17,18,19,20-heptanor-13,14-didehydro-;
3,7-Inter-m-phenylene-16-(p-fluorophenoxy)-4,5,6,17,18,19,20-heptanor-13,14-didehydro-;
3,7-Inter-m-phenylene-16-phenoxy-4,5,6,18,19,20-hexanor-13,14-didehydro-;
3,7-Inter-m-phenylene-16-methyl-16-phenoxy-4,5,6,18,19,20-hexanor-13,14-didehydro-;
3,7-Inter-m-phenylene-4,5,6-trinor-13,14-dihydro-;
3,7-Inter-m-phenylene-4,5,6-trinor-15-methyl-13,14-dihydro-;
3,7-Inter-m-phe-ylene-3-oxa-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-phenylene-17-(m-trifluoromethylphenyl)-4,5,6,18,19,20-hexanor-13,14-dihydro-;
3,7-Inter-m-phenylene-17-(m-chlorophenyl)-4,5,6,18,19,20-hexanor-13,14-dihydro-;
3,7-Inter-m-phenylene-17-(p-fluorophenyl)-4,5,6,18,19,20-hexanor-13,14-dihydro-;
3,7-Inter-m-phenylene-16-methyl-17-phenyl-4,5,6,18,19,20-hexanor-13,14-dihydro-;
3,7-Inter-m-phenylene-16,16-dimethyl-17-phenyl-4,5,6,18,19,20-hexanor-13,14-dihydro-;
3,7-Inter-m-phenylene-16-fluoro-17-phenyl-4,5,6,18,19,20-hexanor-13,14-dihydro-;
3,7-Inter-m-phenylene-16,16-difluoro-17-phenyl-4,5,6,18,19,20-hexanor-13,14-dihydro-;
3,7-Inter-m-phenylene-16-phenyl-4,5,6,17,18,19,20-heptanor-13,14-dihydro-;
3,7-Inter-m-phenylene-16-(m-trifluoromethylphenyl)-4,5,6,17,18,19,20-heptanor-13,14-dihydro-;
3,7-Inter-m-phenylene-16-(m-chlorophenyl)-4,5,6,17,18,19,20-heptanor-13,14-dihydro-;
3,7-Inter-m-phenylene-16-(p-fluorophenyl)-4,5,6,17,18,19,20-heptanor-13,14-dihydro-;
3,7-Inter-m-phenylene-16-phenyl-4,5,6,18,19,20-hexanor-13,14-dihydro-;
3,7-Inter-m-phenylene-16-methyl-16-phenyl-4,5,6,18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,17,18,19,20-heptanor-13,14-dihydro-;
3,7-Inter-m-phenylene-16-(p-fluorophenoxy)-4,5,6,17,18,19,20-heptanor-13,14-dihydro-;
3,7-Inter-m-phenylene-16-methyl-16-phenoxy-4,5,6,18,19,20-hexanor-13,14-dihydro-;
3,7-Inter-m-phenylene-4,5,6-trinor-15-epi-13-cis-;
3,7-Inter-m-phenylene-4,5,6-trinor-15-methyl-15-epi-13-cis-;
3,7-Inter-m-phenylene-4,5,6-trinor-16-methyl-15-epi-13-cis-;
3,7-Inter-m-phenylene-4,5,6-trinor-16,16-dimethyl-15-epi-13-cis-;
3,7-Inter-m-phenylene-4,5,6-trinor-16-fluoro-15-epi-13-cis-;
3,7-Inter-m-phenylene-4,5,6-trinor-16,16-difluoro-15-epi-13-cis-;
3,7-Inter-m-phenylene-17-phenyl-4,5,6,18,19,20-hexanor-15-epi-13-cis-;

3,7-Inter-m-phenylene-17-(m-trifluoromethylphenyl)-4,5,6,18,19,20-hexanor-15-epi-13-cis-;
3,7-Inter-m-phenylene-17-(m-chlorophenyl)-4,5,6,18,19,20-hexanor-15-epi-13-cis-;
3,7-Inter-m-phenylene-17-(p-fluorophenyl)-4,5,6,18,19,20-hexanor-15-epi-13-cis-;
3,7-Inter-m-phenylene-16-methyl-17-phenyl-4,5,6,18,19,20-hexanor-15-epi-13-cis-;
3,7-Inter-m-phenylene-16,16-dimethyl-17-phenyl-4,5,6,18,19,20-hexanor-15-epi-13-cis-;
3,7-Inter-m-phenylene-16-fluoro-17-phenyl-4,5,6,18,19,20-hexanor-15-epi-13-cis-;
3,7-Inter-m-phenylene-16,16-difluoro-17-phenyl-4,5,6,18,19,20-hexanor-15-epi-13-cis-;
3,7-Inter-m-phenylene-16-phenyl-4,5,6,17,18,19,20-heptanor-15-epi-13-cis-;
3,7-Inter-m-phenylene-16-(m-trifluoromethylphenyl)-4,5,6,17,18,19,20-heptanor-15-epi-13-cis-;
3,7-Inter-m-phenylene-16-(m-chlorophenyl)-4,5,6,17,18,19,20-heptanor-15-epi-13-cis-;
3,7-Inter-m-phenylene-16-(p-fluorophenyl)-4,5,6,17,18,19,20-heptanor-15-epi-13-cis-;
3,7-Inter-m-phenylene-16-phenyl-4,5,6,18,19,20-hexanor-15-epi-13-cis-;
3,7-Inter-m-phenylene-16-methyl-16-phenyl-4,5,6,18,19,20-hexanor-15-epi-13-cis-;
3,7-Inter-m-phenylene-16-phenoxy-4,5,6,17,18,19,20-heptanor-15-epi-13-cis-;
3,7-Inter-m-phenylene-16-(m-trifluoromethylphenoxy)-4,5,6,17,18,19,20-heptanor-15-epi-13-cis-;
3,7-Inter-m-phenylene-16-(m-chlorophenoxy)-4,5,6,17,18,19,20-heptanor-15-epi-13-cis-;
3,7-Inter-m-phenylene-16-(p-fluorophenoxy)-4,5,6,17,18,19,20-heptanor-15-epi-13-cis-;
3,7-Inter-m-phenylene-16-phenoxy-4,5,6,18,19,20-hexanor-15-epi-13-cis-;
3,7-Inter-m-phenylene-16-methyl-16-phenoxy-4,5,6,18,19,20-hexanor-15-epi-13-cis-;
3,7-Inter-m-phenylene-3-oxa-4,5,6-trinor-;
3,7-Inter-m-phenylene-3-oxa-4,5,6-trinor-15-methyl-;
3,7-Inter-m-phenylene-3-oxa-4,5,6-trinor-16-methyl-;
3,7-Inter-m-phenylene-3-oxa-4,5,6-trinor-16,16-dimethyl-;
3,7-Inter-m-phenylene-3-oxa-4,5,6-trinor-16-fluoro-;
3,7-Inter-m-phenylene-3-oxa-4,5,6-trinor-16,16-difluoro-;
3,7-Inter-m-phenylene-3-oxa-17-phenyl-4,5,6,18,19,20-hexanor-;
3,7-Inter-m-phenylene-3-oxa-17-(m-trifluoromethylphenyl)-4,5,6,18,19,20-hexanor-;
3,7-Inter-m-phenylene-3-oxa-17-(m-chlorophenyl)-4,5,6,18,19,20-hexanor-;
3,7-Inter-m-phenylene-3-oxa-17-(p-fluorophenyl)-4,5,6,18,19,20-hexanor-;
3,7-Inter-m-phenylene-3-oxa-16-methyl-17-phenyl-4,5,6,18,19,20-hexanor-;
3,7-Inter-m-phenylene-3-oxa-16,16-dimethyl-17-phenyl-4,5,6,18,19,20-hexanor-;
3,7-Inter-m-phenylene-3-oxa-16-fluoro-17-phenyl-4,5,6,18,19,20-hexanor-;
3,7-Inter-m-phenylene-3-oxa-16,16-difluoro-17-phenyl-4,5,6,18,19,20-hexanor-;
3,7-Inter-m-phenylene-3-oxa-16-phenyl-4,5,6,17,18,19,20-heptanor-;
3,7-Inter-m-phenylene-3-oxa-16-(m-trifluoromethylphenyl)-4,5,6,17,18,19,20-heptanor-;
3,7-Inter-m-phenylene-3-oxa-16-(m-chlorophenyl)-4,5,6,17,18,19,20-heptanor-;
3,7-Inter-m-phenylene-3-oxa-16-(p-fluorophenyl)-4,5,6,17,18,19,20-heptanor-;
3,7-Inter-m-phenylene-3-oxa-16-phenyl-4,5,6,18,19,20-hexanor-;
3,7-Inter-m-phenylene-3-oxa-16-methyl-16-phenyl-4,5,6,18,19,20-hexanor-;
3,7-Inter-m-phenylene-3-oxa-16-phenoxy-4,5,6,17,18,19,20-heptanor-;
3,7-Inter-m-phenylene-3-oxa-16-(m-trifluoromethylphenoxy)-4,5,6,17,18,19,20-heptanor-;
3,7-Inter-m-phenylene-3-oxa-16-(m-chlorophenoxy)-4,5,6,17,18,19,20-heptanor-;
3,7-Inter-m-phenylene-3-oxa-16-(p-fluorophenoxy)-4,5,6,17,18,19,20-heptanor-;
3,7-Inter-m-phenylene-3-oxa-16-phenoxy-4,5,6,18,19,20-hexanor-;
3,7-Inter-m-phenylene-3-oxa-16-methyl-16-phenoxy-4,5,6,18,19,20-hexanor-;
3,7-INter-m-phenylene-3-oxa-15-methyl-13,14-didehydro-4,5,6-trinor-;
3,7-Inter-m-phenylene-3-oxa-16-methyl-13,14-didehydro-4,5,6-trinor-;
3,7-Inter-m-phenylene-3-oxa-16,16-dimethyl-13,14-didehydro-4,5,6-trinor-;
3,7-Inter-m-phenylene-3-oxa-16-fluoro-13,14-didehydro-4,5,6-trinor-;
3,7-Inter-m-phenylene-3-oxa-16,16-difluoro-13,14-didehydro-4,5,6-trinor-;
3,7-Inter-m-phenylene-3-oxa-17-phenyl-4,5,6,18,19,20-hexanor-13,14-didehydro-;
3,7-Inter-m-phenylene-3-oxa-17-(m-trifluoromethylphenyl)-4,5,6,18,19,20-hexanor-13,14-didehydro-;
3,7-Inter-m-phenylene-3-oxa-17-(m-chlorophenyl)-4,5,6,18,19,20-hexanor-13,14-didehydro-;
3,7-Inter-m-phenylene-3-oxa-17-(p-fluorophenyl)-4,5,6,18,19,20-hexanor-13,14-didehydro-;
3,7-Inter-m-phenylene-3-oxa-16-methyl-17-phenyl-4,5,6,18,19,20-hexanor-13,14-didehydro-;
3,7-Inter-m-phenylene-3-oxa-16,16-dimethyl-17-phenyl-4,5,6,18,19,20-hexanor-13,14-didehydro-;
3,7-Inter-m-phenylene-3-oxa-16-fluoro-17-phenyl-4,5,6,18,19,20-hexanor-13,14-didehydro-;
3,7-Inter-m-phenylene-3-oxa-16,16-difluoro-17-phenyl-4,5,6,18,19,20-hexanor-13,14-didehydro-;
3,7-Inter-m-phenylene-3-oxa-16-phenyl-4,5,6,17,18,19,20-heptanor-13,14-didehydro-;
3,7-Inter-m-phenylene-3-oxa-16-(m-trifluoromethylphenyl)-4,5,6,17,18,19,20-heptanor-13,14-didehydro-;
3,7-Inter-m-phenylene-3-oxa-16-(m-chlorophenyl)-4,5,6,17,18,19,20-heptanor-13,14-didehydro-;
3,7-Inter-m-phenylene-3-oxa-16-(p-fluorophenyl)-4,5,6,17,18,19,20-heptanor-13,14-didehydro-;
3,7-Inter-m-phenylene-3-oxa-16-phenyl-4,5,6,18,19,20-hexanor-13,14-didehydro-;
3,7-Inter-m-phenylene-3-oxa-16-methyl-16-phenyl-4,5,6,18,19,20-hexanor-13,14-didehydro-;
3,7-Inter-m-phenylene-3-oxa-16-phenoxy-4,5,6,17,18,19,20-heptanor-13,14-didehydro-;
3,7-Inter-m-phenylene-3-oxa-16-(m-trifluoromethylphenoxy)-4,5,6,17,18,19,20-heptanor-13,14-didehydro-;
3,7-Inter-m-phenylene-3-oxa-16-(m-chlorophenoxy)-4,5,6,17,18,19,20-heptanor-13,14-didehydro-;
3,7-Inter-m-phenylene-3-oxa-16-(p-fluorophenoxy)-4,5,6,17,18,19,20-heptanor-13,14-didehydro-;
3,7-Inter-m-phenylene-3-oxa-16-phenoxy-4,5,6,18,19,20-hexanor-13,14-didehydro-;

3,7-Inter-m-phenylene-3-oxa-16-methyl-16-phenoxy-4,5,6,18,19,20-hexanor-13,14-didehydro-;
3,7-Inter-m-phenylene-3-oxa-4,5,6-trinor-13,14-dihydro-;
3,7-Inter-m-phenylene-3-oxa-4,5,6-trinor-15-methyl-13,14-dihydro-;
3,7-Inter-m-phenylene-3-oxa-4,5,6-trinor-16-methyl-13,14-dihydro-;
3,7-Inter-m-phenylene-3-oxa-4,5,6-trinor-16,16-dimethyl-13,14-dihydro-;
3,7-Inter-m-phenylene-3-oxa-4,5,6-trinor-16-fluoro-13,14-dihydro-;
3,7-Inter-m-phenylene-3-oxa-4,5,6-trinor-16,16-difluoro-13,14-dihydro-;
3,7-Inter-m-phenylene-3-oxa-17-phenyl-4,5,6,18,19,20-hexanor-13,14-dihydro-;
3,7-Inter-m-phenylene-3-oxa-17-(m-trifluoromethylphenyl)-4,5,6,18,19,20-hexanor-13,14-dihydro-;
3,7-Inter-m-phenylene-3-oxa-17-(m-chlorophenyl)-4,5,6,18,19,20-hexanor-13,14-dihydro-;
3,7-Inter-m-phenylene-3-oxa-17-(p-fluorophenyl)-4,5,6,18,19,20-hexanor-13,14-dihydro-;
3,7-Inter-m-phenylene-3-oxa-16-methyl-17-phenyl-4,5,6,18,19,20-hexanor-13,14-dihydro-;
3,7-Inter-m-phenylene-3-oxa-16,16-dimethyl-17-phenyl-4,5,6,18,19,20-hexanor-13,14-dihydro-;
3,7-Inter-m-phenylene-3-oxa-16-fluoro-17-phenyl-4,5,6,18,19,20-hexanor-13,14-dihydro-;
3,7-Inter-m-phenylene-3-oxa-16,16-difluoro-17-phenyl-4,5,6,18,19,20-hexanor-13,14-dihydro-;
3,7-Inter-m-phenylene-3-oxa-16-phenyl-4,5,6,17,18,19,20-heptanor-13,14-dihydro-;
3,7-Inter-m-phenylene-3-oxa-16-(m-trifluoromethylphenyl)-4,5,6,17,18,19,20-heptanor-13,14-dihydro-;
3,7-Inter-m-phenylene-3-oxa-16-(m-chlorophenyl)-4,5,6,17,18,19,20-heptanor-13,14-dihydro-;
3,7-Inter-m-phenylene-3-oxa-16-(p-fluorophenyl)-4,5,6,17,18,19,20-heptanor-13,14-dihydro-;
3,7-Inter-m-phenylene-3-oxa-16-phenyl-4,5,6,18,19,20-hexanor-13,14-dihydro-;
3,7-Inter-m-phenylene-3-oxa-16-methyl-16-phenyl-4,5,6,18,19,20-hexanor-13,14-dihydro-;
3,7-Inter-m-phenylene-3-oxa-16-phenoxy-4,5,6,17,18,19,20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18,19,20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-methyl-16-phenoxy-4,5,6,18,19,20-hexanor-13,14-dihydro-;
3,7-Inter-m-phenylene-3-oxa-4,5,6-trinor-15-epi-13-cis-;
3,7-Inter-m-phenylene-3-oxa-4,5,6-trinor-15-methyl-15-epi-13-cis-;
3,7-Inter-m-phenylene-3-oxa-4,5,6-trinor-16-methyl-15-epi-13-cis-;
3,7-Inter-m-phenylene-3-oxa-4,5,6-trinor-16,16-dimethyl-15-epi-13-cis-;
3,7-Inter-m-phenylene-3-oxa-4,5,6-trinor-16-fluoro-15-epi-13-cis-;
3,7-Inter-m-phenylene-3-oxa-4,5,6-trinor-16,16-difluoro-15-epi-13-cis-;
3,7-Inter-m-phenylene-3-oxa-17-phenyl-4,5,6,18,19,20-hexanor-15-epi-13-cis-;
3,7-Inter-m-phenylene-3-oxa-17-(m-trifluoromethylphenyl)-4,5,6,18,19,20-hexanor-15-epi-13-cis-;
3,7-Inter-m-phenylene-3-oxa-17-(m-chlorophenyl)-4,5,6,18,19,20-hexanor-15-epi-13-cis-;
3,7-Inter-m-phenylene-3-oxa-17-(p-fluorophenyl)-4,5,6,18,19,20-hexanor-15-epi-13-cis-;
3,7-Inter-m-phenylene-3-oxa-16-phenoxy-4,5,6,18,19,20-hexanor-15-epi-13-cis-;
3,7-Inter-m-phenylene-3-oxa-16-methyl-17-phenyl-4,5,6,18,19,20-hexanor-15-epi-13-cis-;
3,7-Inter-m-phenylene-3-oxa-16,16-dimethyl-17-phenyl-4,5,6,18,19,20-hexanor-15-epi-13-cis-;
3,7-Inter-m-phenylene-3-oxa-16-fluoro-17-phenyl-4,5,6,18,19,20-hexanor-15-epi-13-cis-;
3,7-Inter-m-phenylene-3-oxa-16,16-difluoro-17-phenyl-4,5,6,18,19,20-hexanor-15-epi-13-cis-;
3,7-Inter-m-phenylene-3-oxa-16-phenyl-4,5,6,17,18,19,20-heptanor-15-epi-13-cis-;
3,7-Inter-m-phenylene-3-oxa-16-(m-trifluoromethylphenyl)-4,5,6,17,18,19,20-heptanor-15-epi-13-cis-;
3,7-Inter-m-phenylene-3-oxa-16-(m-chlorophenyl)-4,5,6,17,18,19,20-heptanor-15-epi-13-cis-;
3,7-Inter-m-phenylene-3-oxa-16-(p-fluorophenyl)-4,5,6,17,18,19,20-heptanor-15-epi-13-cis-;
3,7-Inter-m-phenylene-3-oxa-16-phenyl-4,5,6,18,19,20-hexanor-15-epi-13-cis-;
3,7-Inter-m-phenylene-3-oxa-16-methyl-16-phenyl-4,5,6,18,19,20-hexanor-15-epi-13-cis-;
3,7-Inter-m-phenylene-3-oxa-16-phenoxy-4,5,6,17,18,19,20-heptanor-15-epi-13-cis-;
3,7-Inter-m-phenylene-3-oxa-16-(m-trifluoromethylphenoxy)-4,5,6,17,18,19,20-heptanor-15-epi-13-cis-;
3,7-Inter-m-phenylene-3-oxa-16-(m-chlorophenyl)-4,5,6,17,18,19,20-heptanor-15-epi-13-cis-;
3,7-Inter-m-phenylene-3-oxa-16-(p-fluorophenyl)-4,5,6,17,18,19,20-heptanor-15-epi-13cis-;
3,7-Inter-m-phenylene-3-oxa-16-phenoxy-4,5,6,18,19,20-hexanor-15-epi-13-cis-; and
3,7-Inter-m-phenylene-3-oxa-16-methyl-16-phenoxy-4,5,6,18,19,20-hexanor-15-epi-13-cis-.

EXAMPLE 5 —

2-Decarboxy-2-methylcarbonyl-PGF$_{2\alpha}$ (Formula XXVI: R$_1$ is methyl, Z$_1$ is cis-CH CH-(CH$_2$)$_3$-, R$_8$ is hydroxy, R$_1$ is trans-CH CH-, R$_3$ and R$_4$ of the L$_1$ moiety and R$_5$ of the M$_1$ moiety are all hydrogen, and R$_7$ is n-butyl).

Refer to Chart A.

A. To a solution of 30 g of PGF$_2\alpha$, 11,15-bis(tetrahydropyranyl ether), methyl ester, 190 ml of tetrahydrofuran, and 100 ml of hexamethyldisilizane at ambient temperature is added with stirring 25 ml of trimethylsilyl chloride. The mixture is then allowed to stand at ambient temperature for about one day. When silica gel TLC Rf indicates the C-9 monosilylation is complete, the crude (Formula XXII) product is then concentrated under reduced pressure and the residue taken up in benzene and filtered. Chromatography of the filtrate yields pure Formula XXII compound.

B. Following the procedure of Example 1, Parts A-C, the reaction product of Part A above is transformed to 2-decarboxy-2-alkylcarbonyl-PGF$_2\alpha$, 11,15-bis(tetrahydropyranyl ether).

C. The reaction product of Part B above in a mixture of acetic acid, water, and tetrahydrofuran (20:10:3) is maintained at ambient temperature for about 4 hr. Thereafter the resulting solution is concentrated under reduced pressure, the residue dissolved in methylene chloride, and chromatographed on silica gel. Accordingly there is obtained pure title product.

Following the procedure of Example 5, but employing the appropriate PGF$_2\alpha$-type, 8$\beta$,12$\alpha$-PGF$_2\alpha$-type, PGF$_1\alpha$, 8$\beta$,12$\alpha$-PGF$_1\alpha$-type, PGF$_2\beta$-type, 8$\beta$,12$\alpha$-PGF$_2\beta$-type, PGF$_1\beta$-type, or 8$\beta$, 12$\alpha$-PGF$_1\beta$-type starting material, there are prepared the corresponding
2-decarboxy-2-methylcarbonyl-PGF$_2\alpha$-type;
2-decarboxy-2-methylcarbonyl-8$\beta$,12$\alpha$-PGF$_2\alpha$-type;
2-decarboxy-2-methylcarbonyl-PGF$_1\alpha$-type;
2-decarboxy-2-methylcarbonyl-8$\beta$,12$\alpha$-PGF$_1\alpha$-type;
2-decarboxy-2-methylcarbonyl-PGF$_2\beta$-type;
2-decarboxy-2-methylcarbonyl-8$\beta$,12$\alpha$-PGF$_2\beta$-type;
2-decarboxy-2-methylcarbonyl-PGF$_1\beta$-type; and
2-decarboxy-2-methylcarbonyl-8$\beta$,12$\alpha$-PGF$_1\beta$-type
compounds, either as the respective parent compounds thereof or an analogs thereof exhibiting those specific side chain characteristics described above for the 2-decarboxy-2-methylcarbonyl-9-deoxy-9-methylene-PGF$_2$-type, 2-decarboxy-2-methylcarbonyl-9-deoxy-9-methylene-8$\beta$,12$\alpha$-PGF$_2$-type, 2-decarboxy-2-methylcarbonyl-9-deoxy-9-methylene-PGF$_1$-type, or 2-decarboxy-2-methylcarbonyl-9-deoxy-9-methyl-8$\beta$,12$\alpha$-PGF$_1$-type compounds.

Further, following the procedure of Example 5, but employing the appropriate 11-deoxy-PGF$_2\alpha$-type, 11-deoxy-8$\beta$,12$\alpha$-PGF$_2\alpha$-type, 11-deoxy-PGF$_1\alpha$-type, 11-deoxy-8$\beta$,12$\alpha$-PGF$_1\alpha$-type, 11-deoxy-PGF$_2\beta$-type, 11-deoxy-8$\beta$,12$\alpha$-PGF$_2\beta$-type, 11-deoxy-PGF$_1\beta$-type, or 11-deoxy-8$\beta$,12A-PGF$_1\beta$-type starting material, there are prepared the corresponding
2-decarboxy-2-methylcarbonyl-11-deoxy-PGF$_2\alpha$-type;
2-decarboxy-2-methylcarbonyl-11-deoxy-8$\beta$,12$\alpha$-PGF$_2\alpha$-type;
2-decarboxy-2-methylcarbonyl-11-deoxy-PGF$_1\alpha$-type;
2-decarboxy-2-methylcarbonyl-11-deoxy-8$\beta$,12$\alpha$-PGF$_1\alpha$-type;
2-decarboxy-2-methylcarbonyl-11-deoxy-PGF$_2\beta$-type;
2-decarboxy-2-methylcarbonyl-11-deoxy-8$\beta$,12$\alpha$-PGF$_2\beta$-type;
2-decarboxy-2-methylcarbonyl-11-deoxy-PGF$_1\beta$-type; and
2-decarboxy-2-methylcarbonyl-11-deoxy-8$\beta$,12$\alpha$-PGF$_1\beta$-type
compounds, either as the respective parent compounds thereof or as analogs thereof exhibiting those specific side chain characteristics described above for the 2-decarboxy-2-methylcarbonyl-9-deoxy-9-methylene-PGF$_2$-type, 2-decarboxy-2-methylcarbonyl-9-deoxy-9-methylene-8$\beta$-12$\alpha$-PGF$_2$-type, 2-decarboxy-2-methylcarbonyl-9-deoxy-9-methylene-PGF$_1$-type, 2-decarboxy-2-methylcarbonyl-9-deoxy-9-methylene-8$\beta$,12$\alpha$-PGF$_1$-type compounds.

EXAMPLE 6 —
2-Decarboxy-2-methylcarbonyl-PGE$_2$ (Formula LXXXV: R$_1$, Z$_1$, R$_8$, Y$_1$, M$_1$, L$_1$, and R$_7$ are as defined in Example 5).

Refer to Chart G.
A. A mixture of 30 mg of PGE$_2$, 11,15-bis(tetrahydropyranyl ether), methyl ester, 1 ml of methanol, 25 mg of hydroxylamine hydrochloride, 30 mg of sodium acetate, and 0.5 ml of water was allowed to stand about 18 hr at 25° C. The resulting mixture was then concentrated under a stream of nitrogen at 25° C. The residue was then extracted with dichloromethane, washed, and evaporated to yield a residue. Chromatographing the residue on silica gel yields pure Formula LXXXIII compound: PGE$_2$, 11,15-bis(tetrahydropyranyl ether), methyl ester, oxime.

B. Following the procedure of Example 1, Parts A, B, and C, the reaction product of Part A above is transformed to 2-decarboxy-2-methylcarbonyl-PGE$_2$, 11,15-bis(tetrahydropyranyl ether), oxime.

C. The reaction product of Part B (150 mg) in 10 ml of 90% aqueous acetic acid is cooled to 10° C. and 5 ml of 10% aqueous sodium nitrite is added. The resulting mixture is allowed to stand for 1 hr at 10° C. and thereafter warmed to ambient temperature and treated with 5 ml of 10% aqueous sodium nitrate. The mixture is then allowed to stand an additional 1 hr at ambient temperature and thereafter excess water is added and the resulting mixture extracted with ethyl acetate. These organic extracts are then washed, dried, and concentrated to yield a residue containing pure title product.

Following the procedure of Example 6, but employing the appropriate Formula LXXXII PGE-type, 8$\beta$,12$\alpha$-PGE-type, 11-deoxy-PGE-type, or 8$\beta$,12$\alpha$-11-deoxy-PGE-type starting material, there are prepared.
2-decarboxy-2-methylcarbonyl-PGE-type;
2-decarboxy-2-methylcarbonyl-8$\beta$,12$\alpha$-PGE-type;
2-decarboxy-2-methylcarbonyl-11-deoxy-PGE-type; or
2-decarboxy-2-methylcarbonyl-11-deoxy-8$\beta$,12$\alpha$-PGE-type
compounds either as the parent compounds thereof or exhibiting the side chain characteristics of those compounds described following Example 4.

EXAMPLE 7 —
2-Decarboxy-2-methylcarbonyl-PGA$_2$ (Formula II: D is

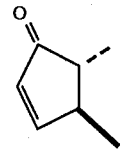

Z$_1$, Y$_1$, M$_1$, L$_1$, and R$_7$ are as defined in Example 5).

A solution of 2-decarboxy-2-methylcarbonyl-PGE$_2$ (300 mg), 4 ml of tetrahydrofuran and 4 ml of 0.5 N. hydrochloric acid is left standing at 25° C. for 5 days. Brine and dichloromethane (1:3) are added and the resulting mixture is stirred. The organic phase is then separated, dried, and concentrated to a residue. The residue is then chromatographed on silica gel yielding pure title products.

Following the procedure of Example 7, but employing the appropriate 2-decarboxy-2-methylcarbonyl-PGE-type or 2-decarboxy-2-methylcarbonyl-8$\beta$,12$\alpha$-PGE-type starting material, there are prepared
2-decarboxy-2-methylcarbonyl-PGA-type; or
2-decarboxy-2-methylcarbonyl-8$\beta$,12$\alpha$-PGA-type
compounds, which exhibit the side chain characteristics described following Example 6 for the various starting material.

EXAMPLE 8 —
2-Decarboxy-2-methylcarbonyl-PGB$_2$ (Formula II: D is

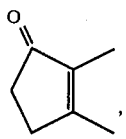

and Z$_1$, Y$_1$, M$_1$, L$_1$, and R$_7$ are as defined in Example 5).

A solution of 2-decarboxy-2-methylcarbonyl-PGE$_2$ in 100 ml of 50% aqueous ethanol containing about 1 g of potassium hydroxide is kept at 25° C. for 10 hr under a nitrogen atmosphere. The resulting solution is then cooled to 10° C. and extracted repeatedly with diethyl ether. The organic extracts are then washed, dried, and concentrated to yield a residue containing the title product. Chromatographing on silica gel yields pure product.

Following the procedure of Example 8, but employing the appropriate 2-decarboxy-2-methylcarbonyl-PGE-type starting material, there are prepared 2-decarboxy-2-methylcarbonyl-PGB-type compounds, which exhibit the side chain characteristics described following Example 6 for the starting material.

EXAMPLE 9 —
2-Decarboxy-2-methylcarbonyl-PGD$_2$ (Formula II: D is

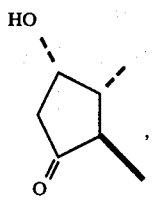

$Z_1$, $Y_1$, $M_1$, $L_1$, and $R_7$ are as defined in Example 5).

Following the procedure of Example 6, PGD$_2$, methyl ester, 15-tetrahydropyranyl ether (the methyl ester of the compound of Example 22, Part B, of U.S. Patent 4,016,814) is transformed to the title product.

Following the procedure of Example 9, but employing the appropriate PGD-type, 8β,12α-type, 9β-PGD-type, or 8β,9β,12α-PGD-type starting material, there are prepared
2-decarboxy-2-methylcarbonyl-PGD-type;
2-decarboxy-2-methylcarbonyl-8β,12α-PGD-type;
2-decarboxy-2-methylcarbonyl-9β-PGD-type; or
2-decarboxy-2-methylcarbonyl-8β,9β,12α-PGD-type
compounds which exhibit the side chain characteristics as the 2-decarboxy-2-methylcarbonyl-PGE-type compounds described following Example 6.

EXAMPLE 10 —
2-Decarboxy-2-methylcarbonyl-9-deoxy-9,10-didehydro-PGD$_2$ (Formula II: D is

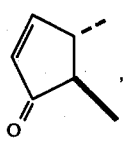

$Z_1$, $Y_1$, $M_1$, $L_1$, and $R_7$ are as defined in Example 5).

Following the procedure of Example 7, 2-decarboxy-2-methylcarbonyl-PGD$_2$ is dehydrated to yield the title product.

Following the procedure of the above examples, but employing the appropriate PGD-type or 8β,12α-PGD-type starting material there are prepared
2-decarboxy-2-methylcarbonyl-9-deoxy-9,10-didehydro-PGD-type; or
2-decarboxy-2-methylcarbonyl-9-deoxy-9,10-didehydro-PGD-type
compounds which exhibit the side chain characteristics described following Example 8 for the corresponding starting material.

Further following the procedures of Examples 5-10, but employing in the ketonization step in place of S-phenyl N-methyl -S-methylsulfoximine the corresponding S-ethylsulfoximine, S-propylsulfoximine, S-isopropylsulfoximine, S-butylsulfoximine, S-isobutylsulfoximine, or S-sec-butylsulfoximine, there are prepared the corresponding 2-decarboxy-2-ethylcarbonyl-, 2-decarboxy-2-propylcarbonyl-, 2-decarboxy-2-isopropylcarbonyl-, 2-decarboxy-2-butylcarbonyl-, 2-decarboxy-2-isobutylcarbonyl-, or 2-decarboxy-2-sec-butylcarbonyl-PG-type products corresponding to the 2-decarboxy-2-methylcarbonyl-PG-type products described in and following Examples 5-10.

Further, in following the procedure of Example 5, but employing the various sulfoximine reagents described in the preceding paragraph and employing in place of the PGFα-type starting material, the corresponding 9-deoxy-9-methylene-PGF compound (i.e., 9-deoxy-9-methylene-PGF$_2$, methyl ester, 11,15-bis(tetrahydropyranyl ether)), there are prepared the corresponding 2-decarboxy-2-ethylcarbonyl-, 2-decarboxy-2-propylcarbonyl-, 2-decarboxy-2-isopropylcarbonyl-, 2-decarboxy-2-butylcarbonyl-, 2-decarboxy-2-isobutylcarbonyl-, or 2-decarboxy-2-sec-butylcarbonyl-9-deoxy-9-methylene-PGF$_2$ products. Further, employing such sulfoximine reagents and the various 9-deoxy-9-methylene-PGF-type or 9-deoxy-9-methylene-8β,12α-PGF-type compounds exhibiting side chain substituents as are described following Example 5 for the corresponding 2-decarboxy-2-methylcarbonyl-PGF$_2$α-type products, the corresponding 2-decarboxy-9-deoxy-9-methylene-PGF-type or 8β,12α-PGF-type products are prepared.

I claim:
1. A prostaglandin analog of the formula

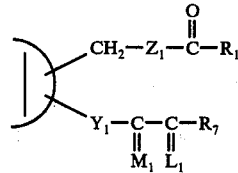

wherein D is

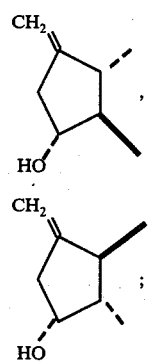

wherein R$_1$ is alkyl of one to 4 carbon atoms, inclusive; wherein L$_1$ is

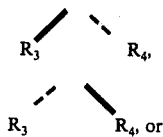

a mixture of

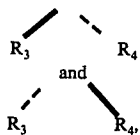

wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

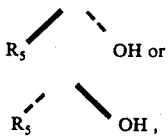

wherein $R_5$ is hydrogen or methyl;
wherein $R_7$ is
  (1) $-(CH_2)_m-CH_3$,

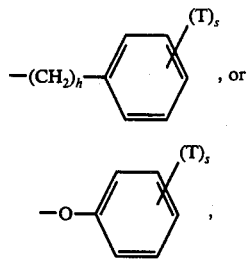

wherein $h$ is zero to three, inclusive,
wherein $m$ is one to 5, inclusive, $s$ is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;
wherein $Y_1$ is
  (1) trans—CH=CH—
  (2) cis—CH=CH—,
  (3) —CH$_2$CH$_2$—, or
  (4) —C≡C—; and
wherein $Z_1$ is
  (1) cis—CH=CH—CH$_2$—(CH$_2$)$_g$—CH$_2$—,
  (2) cis—CH=CH—CH$_2$—(CH$_2$)$_g$—CF$_2$—, (3) cis—CH$_2$—CH=CH—(CH$_2$)$_g$—CH$_2$—,
  (4) —(CH$_2$)$_3$—(CH$_2$)$_g$—CH$_2$—,
  (5) —(CH$_2$)$_3$—(CH$_2$)$_g$—CF$_2$—,
  (6) —CH$_2$—O—CH$_2$—(CH$_2$)$_g$—CH$_2$—,
  (7) —(CH$_2$)$_2$—O—(CH$_2$)$_g$—CH$_2$—,
  (8) —(CH$_2$)$_3$—O—(CH$_2$)$_g$—,
  (9) —C≡C—CH$_2$—(CH$_2$)$_g$—CH$_2$—,
  (10) —CH$_2$—C≡C—(CH$_2$)$_g$—CH$_2$—, or
  (11) trans-(CH$_2$)$_2$—(CH$_2$)$_g$—CH=CH—,
wherein $g$ is one, two, or three.

2. A prostaglandin analog according to claim 1, wherein $R_1$ is methyl.

3. A prostaglandin analog according to claim 2, wherein D is

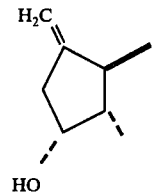

4. 2-Decarboxy-2-methylcarbonyl-9-deoxy-9-methylene-8β,12α-PGF$_2$, a prostaglandin analog according to claim 3.

5. A prostaglandin analog according to claim 2, wherein D is

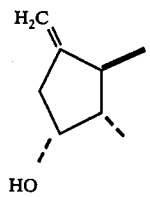

6. A prostaglandin analog according to claim 5, wherein $Y_1$ is cis—CH=CH—.

7. 2-Decarboxy-2-methylcarbonyl-9-deoxy-9-methylene-13-cis-PGF$_2$, a prostaglandin analog according to claim 6.

8. A prostaglandin analog according to claim 5, wherein $Y_1$ is —CH$_2$CH$_2$—.

9. 2-Decarboxy-2-methylcarbonyl-9-deoxy-9-methylene-13,14-dihydro-PGF$_2$, a prostglandin analog according to claim 8.

10. A prostaglandin analog according to claim 5, wherein $Y_1$ is —C≡C—.

11. 2-Decarboxy-2-methylcarbonyl-9-deoxy-9-methylene-13,14-didehydro-PGF$_2$, a prostaglandin analog according to claim 10.

12. A prostaglandin analog according to claim 5, wherein $Y_1$ is trans—CH=CH—.

13. A prostaglandin analog according to claim 12, wherein $R_7$ is

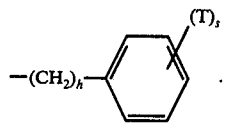

14. 2-Decarboxy-2-methylcarbonyl-9-deoxy-9-methylene-17-phenyl-18,19,20-trinor-PGF$_2$, a prostaglandin analog according to claim 13.

15. A prostaglandin analog according to claim 12, wherein $R_7$ is

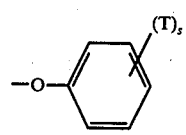

16. 2-Decarboxy-2-methylcarbonyl-9-deoxy-9-methylene-16-phenoxy-17,18,19,20-tetranor-PGF$_2$, a prostaglandin analog according to claim 15.

17. A prostaglandin analog according to claim 12, wherein R$_7$ is —(CH$_2$)$_m$—CH$_3$—.

18. A prostaglandin analog according to claim 17, wherein Z$_1$ is cis—CH=CH—CH$_2$—(CH$_2$)$_g$—CF$_2$—.

19. 2-Decarboxy-2-methylcarbonyl-9-deoxy-9-methylene-2,2-difluoro-PGF$_2$, a prostaglandin analog according to claim 18.

20. A prostaglandin analog according to claim 17, wherein Z$_1$ is cis—CH$_2$—CH=CH—(CH$_2$)$_g$—CH$_2$—.

21. 2-Decarboxy-2-methylcarbonyl-9-deoxy-9-methylene-cis-4,5-didehydro-16,16-dimethyl-PGF$_2$, a prostaglandin analog according to claim 20.

22. A prostaglandin analog according to claim 17, wherein Z$_1$ is —(CH$_2$)$_3$—(CH$_2$)$_g$—CH$_2$—.

23. 2-Decarboxy-2-methylcarbonyl-9-deoxy-9-methylene-PGF$_1$, a prostaglandin analog according to claim 22.

24. A prostaglandin analog according to claim 17, wherein Z$_1$ is —(CH$_2$)$_3$—(CH$_2$)$_q$—CF$_2$—.

25. 2-Decarboxy-2-methylcarbonyl-9-deoxy-9-methylene-2,2-difluoro-PGF$_1$, a prostaglandin analog according to claim 24.

26. A prostaglandin analog according to claim 17, wherein Z$_1$ is —CH$_2$—O—CH$_2$—(CH$_2$)$_g$—CH$_2$—.

27. 2-Decarboxy-2-methylcarbonyl-9-deoxy-9-methylene-5-oxa-PGF$_1$, a prostaglandin analog according to claim 26.

28. A prostaglandin analog according to claim 17, wherein Z$_1$ is —(CH$_2$)$_2$—O—(CH$_2$)$_g$—CH$_2$—.

29. 2-Decarboxy-2-methylcarbonyl-9-deoxy-9-methylene-4-oxa-PGF$_1$, a prostaglandin analog according to claim 28.

30. A prostaglandin analog according to claim 17, wherein Z$_1$ is —(CH$_2$)$_3$—O—(CH$_2$)$_g$—.

31. 2-Decarboxy-2-methylcarbonyl-9-deoxy-9-methylene-3-oxa-PGF$_1$, a prostaglandin analog according to claim 30.

32. A prostaglandin analog according to claim 17, wherein Z$_1$ is —C≡C—CH$_2$—(CH$_2$)$_g$—CH$_2$—.

33. 2-Decarboxy-2-methylcarbonyl-9-deoxy-9-methylene-5,6-didehydro-PGF$_2$, a prostaglandin analog according to claim 32.

34. A prostaglandin analog according to claim 17, wherein Z$_1$ is —CH$_2$—C≡C—(CH$_2$)$_q$—CH$_2$—.

35. 2-Decarboxy-2-methylcarbonyl-9-deoxy-9-methylene-4,4,5,5-tetradehydro-PGF$_1$, a prostaglandin analog according to claim 34.

36. A prostaglandin analog according to claim 17, wherein Z$_1$ is trans-(CH$_2$)$_2$—(CH$_2$)$_g$—CH=CH—.

37. 2-Decarboxy-2-methylcarbonyl-9-deoxy-9-methylene-trans-2,3-didehydro-PGF$_1$, a prostaglandin analog according to claim 36.

38. A prostaglandin analog according to claim 17, wherein Z$_1$ is cis—CH=CH—CH$_2$—(CH$_2$)$_g$—CH$_2$.

39. A prostaglandin analog according to claim 38, wherein R$_5$ is methyl.

40. 2-Decarboxy-2-methylcarbonyl-9-deoxy-9-methylene-15-methyl-PGF$_2$, a prostaglandin analog according to claim 38.

41. A prostaglandin analog according to claim 38, wherein R$_5$ is hydrogen.

42. A prostaglandin analog according to claim 41, wherein one of R$_3$ and R$_4$ is fluoro.

43. 2-Decarboxy-2-methylcarbonyl-9-deoxy-9-methylene-16,16-difluoro-PGF$_2$, a prostaglandin analog according to claim 42.

44. A prostaglandin analog according to claim 41, wherein at least one of R$_3$ and R$_4$ is methyl.

45. 2-Decarboxy-2-methylcarbonyl-9-deoxy-9-methylene-16,16-dimethyl-PGF$_2$, a prostaglandin analog according to claim 44.

46. A prostaglandin analog according to claim 41, wherein R$_3$ and R$_4$ are both hydrogen.

47. 2-Decarboxy-2-methylcarbonyl-9-deoxy-9-methylene-PGF$_2$, a prostaglandin analog according to claim 46.

* * * * *

UNITED STATES PATENT OFFICE
CERTIFICATE OF CORRECTION

Patent No. 4,123,463                    Dated 31 October 1978

Inventor(s) Gordon L. Bundy

It is certified that error appears in the above-identified patent and that said Letters Patent are hereby corrected as shown below:

Column 4, lines 1-7,

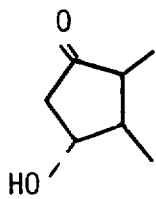  should read  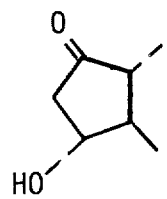  ;

Column 6, line 44, "trans-(CH=CH-" should read -- trans-CH=CH- --; line 53, "-(CH$_2$)$_3$-(CH$_2$)q-CF$_2$-" should read -- -(CH$_2$)$_3$-(CH$_2$)g-CF$_2$- --;

Column 7, lines 62-68,

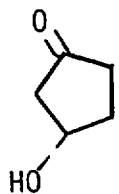  should read  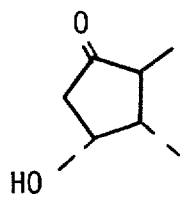  ;

Column 14, line 29, "noxious atent" should read -- noxious agent --; lines 37-46, should read as follows:

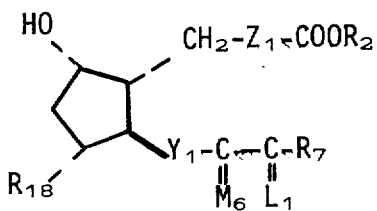

Column 19, lines 54-55, "hydroxy of hydrogen" should read -- hydroxy or hydrogen --;
Column 20, line 60, "2-decaroboxy-2-" should read -- 2-decarboxy-2- --;
Column 21, line 59, "8,12-PG-type" should read -- 8β,12α-PG-type --;

UNITED STATES PATENT OFFICE
CERTIFICATE OF CORRECTION

Patent No. 4,123,463             Dated 31 October 1978

Inventor(s) Gordon L. Bundy

It is certified that error appears in the above-identified patent and that said Letters Patent are hereby corrected as shown below:

Column 22, lines 60-61, "2-decarboxy-2-(alkylcarbonyl-PGFα-" should read -- 2-decarboxy-2-(alkylcarbonyl)-PGFα- --;

Column 25, lines 59-60, "rendering is suitable" should read -- rendering it suitable --;

Column 26, line 65, "zylane" should read -- xylane --;

Column 29, line 1, "18,19,2+-trinor-" should read -- 18,19,20-trinor- --; lines 34-35, "13,14-didehydro-;" should read -- 13,14-didehydro- --;

Column 32, lines 22-23, "18,19,20-trinor-13-cis-;" should read -- 18,19,20-trinor-15-epi-13-cis-; --;

Column 36, line 36, "2,2-16,16-dimethyl-" should read -- 2,2-Difluoro-16,16-dimethyl- --;

Column 37, line 47, "1-,19,20-trinor-" should read -- 18,19,20-trinor- --

Column 58, line 10, "3,7-Inter-m-phe ylene-3-oxa-4,5,6-trinor-" should read -- 3,7-Inter-m-phenylene-4,5,6-trinor- --;

Column 62, line 42, "cis-CH CH-(CH$_2$)$_3$-" should read -- cis-CH=CH-(CH$_2$)$_3$- --; line 43, "trans-CH CH-," should read -- trans-CH=CH-, --;

Column 63, line 28, "11-deoxy-8β,12A-PGF$_1$β-" should read -- 11-deoxy-8β,12α-PGF$_1$β- --;

Column 65, lines 67-68, "9,10-didehydro-PGB-type" should read -- 9,10-didehydro-8β,12α-PGD-type --;

Column 67, line 61, "-(CH$_2$)$_3$-(CH$_2$)q-CF$_2$-" should read -- -(CH$_2$)$_3$-(CH$_2$)g-CF$_2$- --;

Column 68, lines 20-28,

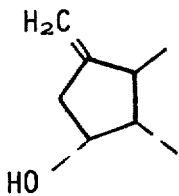     should read     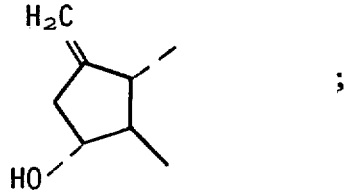    ;

UNITED STATES PATENT OFFICE
CERTIFICATE OF CORRECTION

Patent No. 4,123,463          Dated 31 October 1978

Inventor(s) Gordon L. Bundy

It is certified that error appears in the above-identified patent and that said Letters Patent are hereby corrected as shown below:

Column 69, line 22, "$-(CH_2)_3-(CH_2)q-CF_2-$" should read -- $-(CH_2)_3-(CH_2)g-CF_2-$ --;
Column 70, line 7, "$-CH_2-C\equiv C-(CH_2)q-CH_2-$" should read -- $-CH_2-C\equiv C-(CH_2)g-CH_2-$ --; line 22, "according to claim 38" should read -- according to claim 39 --.

Signed and Sealed this

Twenty-ninth Day of September 1981

[SEAL]

Attest:

GERALD J. MOSSINGHOFF

Attesting Officer     Commissioner of Patents and Trademarks